United States Patent [19]

Schmidt et al.

[11] Patent Number: 4,734,407
[45] Date of Patent: Mar. 29, 1988

[54] ALPHA-AMINOACYL-PENICILLINS AND CEPHALOSPORINS

[75] Inventors: Gunter Schmidt, Wuppertal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 838,236

[22] Filed: Mar. 10, 1986

[30] Foreign Application Priority Data

Mar. 16, 1985 [DE] Fed. Rep. of Germany ....... 3509618

[51] Int. Cl.$^4$ .................. A61K 31/43; A61K 31/545; C07D 501/14; C07D 499/46
[52] U.S. Cl. .................... 514/196; 514/194; 514/201; 514/202; 514/203; 514/204; 514/205; 514/206; 540/221; 540/222; 540/223; 540/225; 540/227; 540/228; 540/328
[58] Field of Search ................ 260/239.1; 544/21, 23, 544/25, 27, 28; 514/194, 196, 201, 202, 203, 205, 206, 204; 540/221, 328, 223, 225, 227, 228, 222

[56] References Cited

U.S. PATENT DOCUMENTS

| | | | |
|---|---|---|---|
| 3,080,356 | 3/1963 | Catlin et al. | 260/239.1 |
| 4,317,775 | 3/1982 | Burri et al. | 260/239.1 |
| 4,395,412 | 7/1983 | Saikawa et al. | 544/21 X |
| 4,461,767 | 7/1984 | Breuer et al. | 514/202 |
| 4,496,560 | 1/1985 | Farge et al. | 514/204 |
| 4,537,886 | 8/1985 | Taylor et al. | 514/193 |

FOREIGN PATENT DOCUMENTS

| | | |
|---|---|---|
| 2408698 | 9/1974 | Fed. Rep. of Germany . |
| 2728578 | 1/1978 | Fed. Rep. of Germany . |
| 938321 | 10/1963 | United Kingdom . |
| 1174335 | 12/1969 | United Kingdom . |

*Primary Examiner*—Werren B. Lone
*Assistant Examiner*—Vera C. Clarke
*Attorney, Agent, or Firm*—Sprung Horn Kramer & Woods

[57] ABSTRACT

Antibacterially active and animal growth-regulating novel $\beta$-lactam compounds of the formula

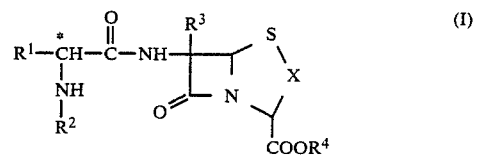

in which
$R^1$ represents an optionally substituted radical of the formula

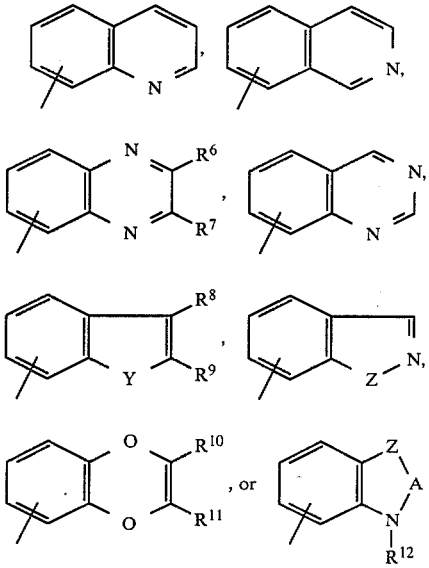

Z represents oxygen, sulphur or $-N-R^{13}$, and
A represents the group

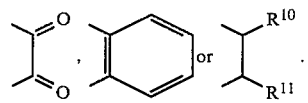

20 Claims, No Drawings

ALPHA-AMINOACYL-PENICILLINS AND CEPHALOSPORINS

The invention relates to β-lactam antibiotics, processes for their preparation and their use in medicaments, in particular as antibiotics with an oral action.

Various α-aminoacyl-cephalosporin and -penicillin antibiotics are already known, thus, for example, cefalexin (British Patent Specification No. 1,174,335), cefaclor [DE-OS (German Published Specification) Nos. 2,408,698 and 2,728,578], ampicillin (British Patent Specification No. 938,321) and amoxicillin (British Patent Specification No. 1,339,605).

The invention relates to β-lactam compounds of the general formula I

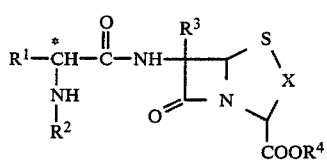

in which
X represents a radical of the formula

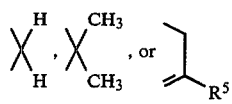

wherein
$R^5$ represents hydrogen, or represents halogen, azido or represents straight-chain, branched or cyclic, saturated or unsaturated alkyl which has up to 6 C atoms and is optionally substituted by halogen, $OCONH_2$, $C_1$–$C_5$-alkoxy, $C_1$–$C_5$-alkylthio, $C_2$–$C_7$-acyloxy, by a pyridinium radical, which can be mono- or polysubstituted, or by a radical of the formula

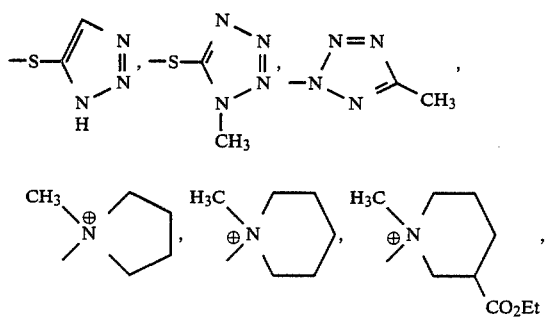

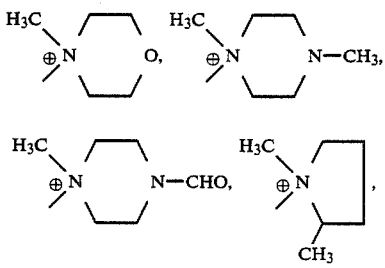

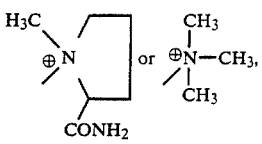

or represents alkoxy or alkylthio with up to 5 C atoms,
$R^1$ represents an optionally substituted radical of the formula

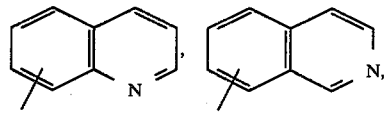

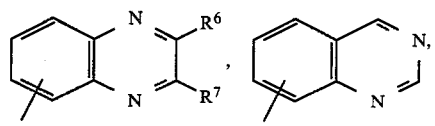

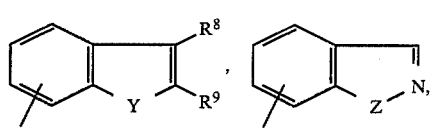

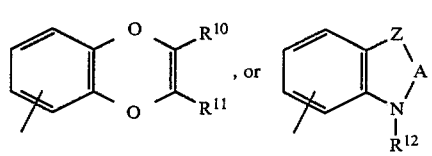

wherein
$R^6$ and $R^7$ are identical or different and represent hydrogen, or represent optionally substituted $C_6$–$C_{10}$-aryl, or represent an optionally substituted amino group, or represent hydroxyl, or represent alkoxy with up to 8 C atoms, or represent acyl or acyloxy with in each case up to 7 C atoms, or represent optionally substituted alkyl with up to 12 C atoms, $R^8$ and $R^9$ are identical or different and represent hydrogen, or represent optionally substituted $C_6$–$C_{10}$-aryl, or represent heterocyclyl, or represent hydroxyl, or represent an optionally substituted amino group, or represent alkoxy with up to 8 C atoms, or represent acyl with up to 7 C atoms, or represent acyloxy with up to 7 C atoms, or represent alkoxycarbonyl with up to 8 C atoms, or represent optionally substituted alkyl with up to 12 C atoms, or $R^8$ and $R^9$ together represent the group

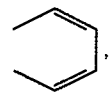

$R^{10}$ and $R^{11}$ are identical or different and represent hydrogen, or represent optionally substituted alkyl with up to 12 C atoms, or represent optionally substituted $C_6$–$C_{10}$-aryl, or represent alkoxycarbonyl with up to 8 C atoms,
Y represents oxygen or —N—$R^{12}$,
Z represents oxygen, sulphur or —N—$R^{13}$,
A represents the group

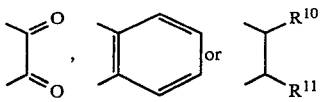

and wherein $R^{12}$ and $R^{13}$ are identical or different and represent hydrogen, or represent optionally substituted $C_6$–$C_{10}$-aryl, or represent straight-chain, branched or cyclic alkyl with up to 8 C atoms, $R^2$ represents hydrogen or represents an amino-protective group, $R^3$ represents hydrogen, or represents alkoxy or alkylthio with in each case up to 5 C atoms, or represents an optionally substituted amino group, or represents NHCHO, $R^4$ represents hydrogen, or represents a carboxyl-protective group, or represents alkali metal ions or ammonium ions, or represents a radical of the formula

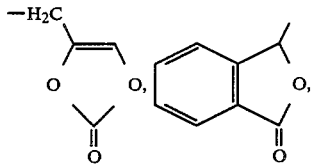

$-CH_2-O-CO-C(CH_3)_3$ or $-CH(CH_3)-O-CO-O-C_2H_5$.

If $R^1$ is substituted, it is substituted in the carbocyclic and/or heterocyclic ring. In this case, $R^1$ is mono-, di-, tri- or tetra-substituted, preferably mono- or di-substituted, by halogen, preferably fluorine, chlorine or bromine, or by alkyl, alkoxy, alkylthio, halogenoalkyl, halogenoalkoxy or halogenoalkylthio (alkyl with in each case up to 8 C atoms, preferably with up to 6 C atoms), particularly preferably alkyl, alkylthio or alkoxy with in each case up to 4 C atoms, trifluoromethyl, trifluoromethoxy, trifluoromethylthio, nitro, cyano or phenyl.

If $R^2$ represents an amino-protective group, these are those which are customary in β-lactam chemistry, such as, for example, tert.-butoxycarbonyl (Boc), carbobenzoxy (Cbz), trityl (Trt), benzyl (Bzl), benzyloxycarbonyl (Z), formyl, chloroacetyl or 2-methoxycarbonyl-1-methylvinyl.

If $R^4$ represents a carboxyl-protective group, these are preferably protective groups which can easily be split off, such as, for example, tert.-butyl, decyl, 2,2,2-trichloroethyl, benzyl, 4-methoxybenzyl, 4-nitrobenzyl, triphenylmethyl, diphenylmethyl, acetoxymethyl, pivaloyloxymethyl, allyl or trimethylsilyl.

Optionally substituted aryl in general represents phenyl which is mono-, di-, tri- or tetra-substituted, preferably mono-, di- or tri-substituted, by identical or different substituents, substituents which may be mentioned being: halogen, preferably fluorine, chlorine and bromine, alkyl, alkoxy and alkylthio with in each case up to 10 C atoms, preferably up to 6 C atoms, halogenoalkyl, halogenoalkoxy and halogenoalkylthio with in each case up to 7 C atoms, preferably up to 5 C atoms, nitro, cyano, benzyl, $SO_3H$, amidino, $SO_2$-alkyl with up to 4 C atoms, $SO_2NH_2$ and an optionally substituted amino group.

Optionally substituted alkyl in general represents straight-chain, branched or cyclic, saturated or unsaturated alkyl with preferably up to 10 C atoms, possible substituents being: halogen, alkoxy and alkylthio with in each case up to 8 C atoms, preferably with up to 6 C atoms, halogenoalkylthio and halogenoalkoxy with in each case up to 8 C atoms, preferably with up to 6 C atoms, nitro, cyano, an optionally substituted amino group, optionally substituted aryl, $SO_3H$, $SO_2NH_2$, $SO_2$-alkyl with up to 6 C atoms, preferably with up to 4 C atoms, OH, SH, acyloxy and acylthio with in each case up to 7 C atoms, OCONH_2, carboxyl, alkoxycarbonyl with up to 8 C atoms, preferably with up to 6 C atoms, phenyloxy, phenylthio, benzyloxy and benzylthio.

An optionally substituted amino group represents the radical of the formula

wherein $R^{14}$ and $R^{15}$ are identical or different and represent hydrogen, or represent alkyl with up to 10 C atoms, preferably with up to 6 C atoms and particularly preferably with up to 4 C atoms, or represent $C_6$–$C_{10}$-aryl, preferably phenyl, or represent $C_7$–$C_{14}$-aralkyl, preferably $C_7$–$C_{10}$-aralkyl and particularly preferably benzyl, or represent acyl with up to 10 C atoms, preferably up to 8 C atoms and particularly preferably benzoyl or acetyl. Preferred compounds of the formula I are those in which X represents a radical of the formula

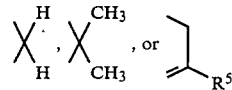

wherein $R^5$ represents hydrogen, or represents fluorine, chlorine or bromine, or represents straight-chain, branched or cyclic, saturated or unsaturated alkyl which has up to 4 C atoms and is optionally substituted by one or more radicals from the group comprising fluorine, chlorine, bromine, alkoxy and alkylthio with in each case up to 3 C atoms, $OCONH_2$ and acyloxy with up to 4 C atoms, or by a radical of the formula

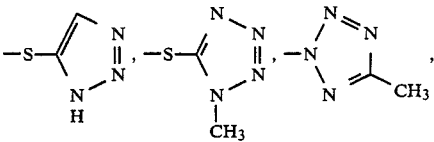

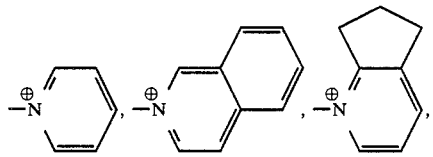

-continued

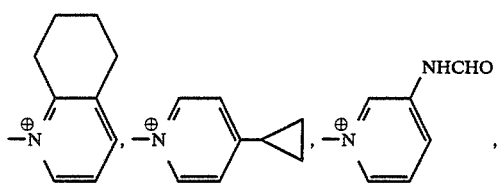

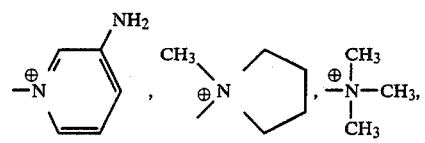

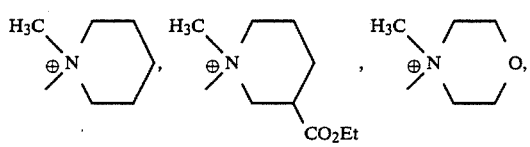

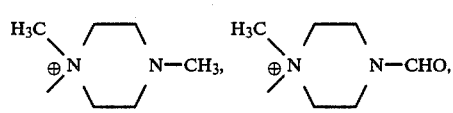

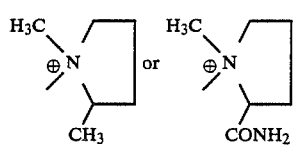

or represents alkoxy or alkylthio with in each case up to 3 C atoms, $R^1$ represents an optionally substituted radical of the formula

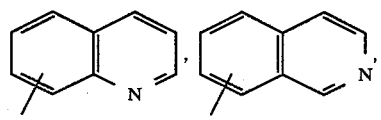

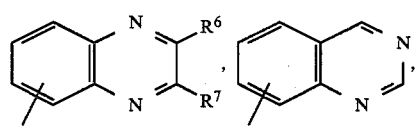

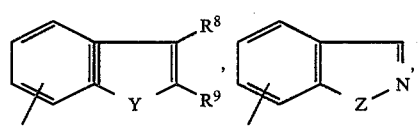

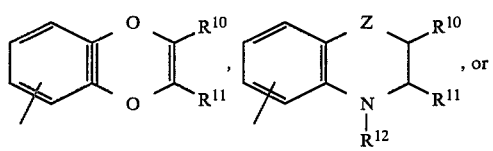

-continued

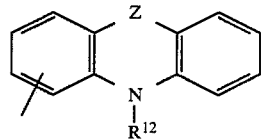

wherein $R^6$ and $R^7$ are identical or different and represent hydrogen, or represent phenyl, which is optionally mono- or di-substituted by identical or different substituents from the group comprising fluorine, chlorine, bromine, alkyl, alkoxy and alkylthio with in each case up to 4 C atoms and halogenoalkyl, halogenoalkoxy and halogenoalkylthio with in each case up to 3 C atoms and with one or more fluorine radicals, or by nitro, cyano, amino or dimethylamino, or represent an optionally substituted amino group with the abovementioned meaning, or represent hydroxyl, or represent alkoxy with up to 6 C atoms, or represent benzoyloxy or alkanoyloxy with up to 4 C atoms, or represent straight-chain, branched or cyclic, saturated or unsaturated alkyl which has up to 8 C atoms and is optionally substituted by one or more substituents from the group comprising fluorine, chlorine, bromine, alkoxy and alkylthio with in each case up to 4 C atoms, halogenoalkoxy and halogenoalkylthio with in each case up to 4 C atoms and one or more fluorine atoms, nitro, cyano, an optionally substituted amono group with the abovementioned meaning, phenyl, $SO_3H$, $SO_2NH_2$, $SO_2$-alkyl with up to 2 C atoms, OH, SH, benzoyloxy, alkanoyloxy with up to 4 C atoms, $OCONH_2$ and alkoxycarbonyl with up to 4 C atoms, $R^8$ and $R^9$ are identical or different and represent hydrogen, or represent phenyl, which is optionally mono- or di-substituted by identical or different substituents from the group comprising fluorine, chlorine, bromine, alkyl, alkoxy and alkylthio with in each case up to 4 C atoms and halogenoalkyl, halogenoalkoxy and halogenoalkylthio with in each case up to 3 C atoms and with one or more fluorine atoms, or by nitro, cyano, dimethylamino or amino, or represent hydroxyl, or represent pyridyl, thienyl, furyl or pyrimidyl, or represent an optionally substituted amino group with the abovementioned meaning, or represent alkoxy with up to 6 C atoms, or represent benzoyloxy or alkanoyloxy with up to 4 C atoms, or represent benzoyl (optionally substituted phenyl) or acetyl, or represent alkoxycarbonyl with up to 6 Catoms, or represent straight-chain, branched or cyclic, saturated or unsaturated alkyl which has up to 8 C atoms and is optionally substituted by one or more substituents from the group comprising fluorine, chlorine, bromine, alkoxy and alkylthio with in each case up to 4 C atoms, halogenoalkoxy and halogenoalkylthio with in each case up to 4 C atoms and with one or more fluorine atoms, nitro, cyano, an optionally substituted amino group with the abovementioned meaning, phenyl, $SO_3H$, $SO_2NH_2$, $SO_2$-alkyl with up to 2 C atoms, OH, SH, benzoyloxy, alkanoyloxy with up to 4 C atoms, $OCONH_2$, alkoxycarbonyl with up to 4 C atoms, phenyloxy, phenylthio, benzyloxy and benzylthio, or $R^8$ and $R^9$ together represent the group

R¹⁰ and R¹¹ are identical or different and represent hydrogen, or represent straight-chain, branched or cyclic, saturated or unsaturated alkyl which has up to 8 C atoms and is optionally substituted by one or more substituents from the group comprising fluorine, chlorine, bromine, alkoxy and alkylthio with in each case up to 4 C atoms, halogenalkoxy and halogenalkylthio with in each case up to 4 C atoms and with one or more fluorine atoms, nitro, cyano, an optionally substituted amino group with the abovementioned meaning, phenyl, SO₃H, SO₂NH₂, SO₂-alkyl with up to 2 C atoms, OH, SH, benzoyloxy, alkanoyloxy with up to 4 C atoms, OCONH₂ and alkoxycarbonyl with up to 4 C atoms, or represent phenyl, which is optionally mono- or disubstituted by identical or different substituents from the group comprising fluorine, chlorine, bromine, alkyl, alkoxy and alkylthio with in each case up to 4 C atoms, halogenoalkyl, halogenoalkoxy and halogenoalkylthio with in each case up to 3 C atoms and with one or more fluorine atoms, nitro, cyano, amino and dimethylamino, or represent alkoxycarbonyl with up to 6 C atoms, Y represents oxygen or —N—R¹²

Z represents oxygen, sulphur or —NR¹³, and wherein

R¹² and R¹³ are identical or different and represent hydrogen, or represent phenyl, or represent straight-chain, branched or cyclic alkyl with up to 6 C atoms, R² represents hydrogen or represents an amino protective group, R³ represents hydrogen, or represents alkoxy or alkylthio with in each case up to 3 C atoms, or represents an optionally substituted amino group with the abovementioned meaning, or represents NHCHO, and R⁴ represents hydrogen, or represents a carboxyl-protective group, or represents sodium, potassium, lithium or ammonium ions, or represents a radical of the formula

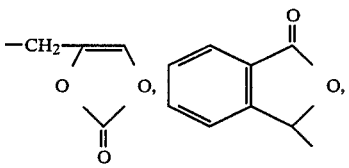

CH₂—O—CO—C(CH₃)₃ or —CH(CH₃)—O—CO—O—C₂H₅.

Particularly preferred compounds of the formula I are those in which

X represents a radical of the formula

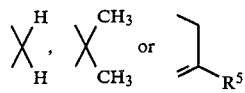

wherein

R⁵ represents hydrogen, or represents chlorine or fluorine, or represents methyl, methoxy, methylthio, trifluoromethyl or methoxymethyl, or represents vinyl, —CH=CH—CH₃, —CH=CH—C₂H₅, —CH=CH—CH₂Cl,

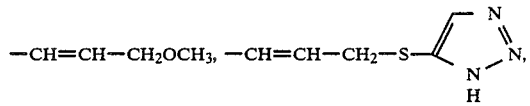

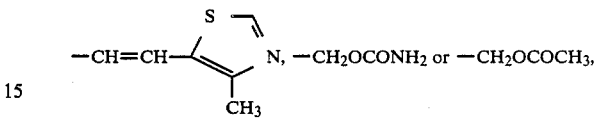

or represents a radical of the formula

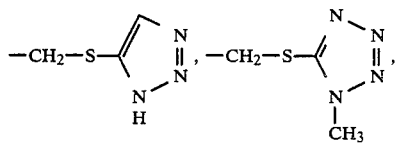

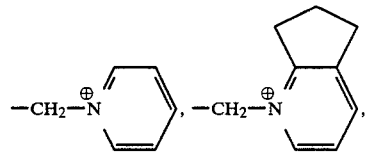

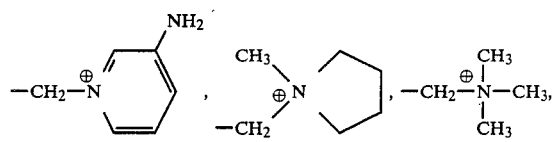

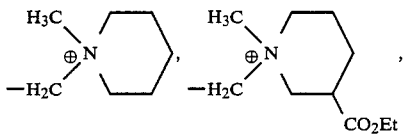

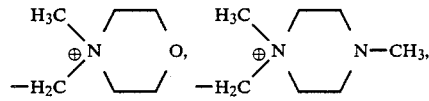

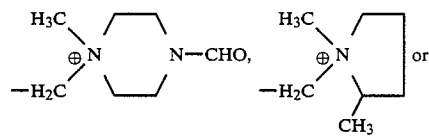

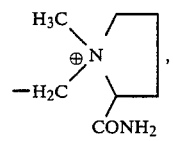

R¹ represents an optionally substituted radical of the formula

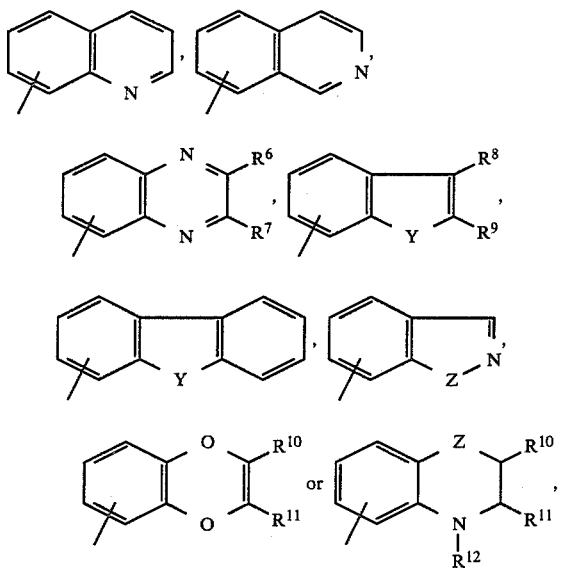

wherein

R⁶ and R⁷ are identical or different and represent hydrogen, or represent phenyl, which is optionally monosubstituted by chlorine, fluorine, alkyl with up to 4 C atoms, methoxy, methylthio, trifluoromethyl, trifluoromethoxy, trifluoromethylthio, nitro, cyano, amino or dimethylamino, or represent amino, methylamino, dimethylamino, phenylamino or acetylamino, or represent hydroxyl, or represent alkoxy with up to 4 C atoms, or represent benzoyloxy or acetyloxy, or represent straight-chain, branched or cyclic, saturated or unsaturated alkyl which has up to 6 C atoms and is optionally substituted by one or more substituents from the group comprising fluorine, chlorine, methoxy, methylthio, trifluoromethoxy and cyano, R⁸ and R⁹ are identical or different and represent hydrogen, or represent phenyl, which is optionally substituted by fluorine, chlorine, alkyl with up to 4 C atoms, methoxy, methylthio, trifluoromethyl, trifluoromethoxy, trifluoromethylthio, nitro, cyano, amino or dimethylamino, or represent pyridyl, thienyl, furyl or pyrimidyl, or represent hydroxyl, or represent amino, methylamino, dimethylamino, phenylamino or acetylamino, or represent alkoxy with up to 4 C atoms, or represent benzoyloxy or acetyloxy, or represent benzoyl or acetyl, or represent alkoxycarbonyl with up to 4 C atoms, or represent straight-chain, branched or cyclic, saturated or unsaturated alkyl which has up to 6 C atoms and is optionally substituted by one or more substituents from the group comprising fluorine, chlorine, methoxy, methylthio, trifluoromethoxy, cyano, phenyloxy and benzyloxy, R¹⁰ and R¹¹ are identical or different and represent hydrogen, or represent straight-chain, branched or cyclic, saturated or unsaturated alkyl which has up to 6 C atoms and is optionally substituted by one or more substituents from the group comprising fluorine, chlorine, methoxy, methylthio, trifluoromethoxy and cyano, or represent phenyl, which is optionally substituted by fluorine, chlorine, alkyl with up to 4 C atoms, methoxy, methylthio, trifluoromethyl, trifluoromethoxy, trifluoromethylthio, nitro, cyano, amino or dimethylamino, or represent alkoxycarbonyl with up to 4 C atoms, Y represents oxygen or NR¹², Z represents oxygen, sulphur or —NR¹³, and wherein R¹² and R¹³ are identical or different and represent hydrogen, or represent phenyl, or represent straight-chain or branched alkyl with up to 4 C atoms, R² represents hydrogen, or represents an amino-protective group, R³ represents hydrogen, or represents methoxy or methylthio, or represents amino, alkylamino or dialkylamino, alkyl with in each case up to 3 C atoms, phenylamino, benzylamino or acetylamino, or represents NHCHO, and R⁴ represents hydrogen, or represents a carboxyl-protective group, or represents sodium, potassium, lithium or ammonium ions, or represents a radical of the formula

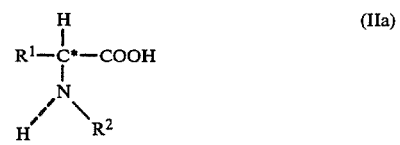

—CH₂—O—CO—C(CH₃)₃ or —CH(CH₃)—O—CO—O—C₂H₅.

The terms amino-protective group and carboxyl-protective group have the meaning already given above.

The compounds of the formula I can be in the form of free acids, esters, inner salts or non-toxic pharmaceutically acceptable salts of the acid carboxyl groups, such as sodium, potassium, magnesium, calcium, aluminum and ammonium salts and non-toxic substituted ammonium salts, with amines, such as di- and tri-lower alkylamines, procaine, dibenzylamine, N,N'-dibenzylethylenediamine, N-benzyl-β-phenyl-ethylamine, N-methyl- and N-ethylmorpholine, 1-ephenamine, dehydroabietylamine, N,N'-bis-dehydroabietylethylenediamine, N-lower-alkylpiperidines and other amines which can be used for the formation of salts of penicillins and cephalosporins.

Because of the presence of the asymmetric carbon atom labelled *, the new β-lactam antibiotics of the formula I include the D-, L- and D,L-forms. The D-forms of the compounds of the general formula I according to the invention are preferred.

Both the diastereomer mixtures and the D-form and L-form of the compounds according to the invention can be used for the treatment of bacterial infection diseases.

The compounds of the general formula I are obtained by a process in which compounds of the general formula IIa $$R^1-\underset{\underset{H}{|}}{\overset{\overset{H}{|}}{C^*}}-COOH \quad \text{(IIa)}$$
$$\underset{R^2}{\overset{|}{N}}$$

in which

R¹ has the abovementioned meaning and in which $R^2$ represents an amino-protective group, after activation of the carboxyl group by conversion into a mixed anhydride, for example with pivaloyl chloride or ethyl or isobutyl chloroformate, after conversion into the mesylate by means of methanesulphonyl chloride or after conversion into an activated ester, for example with 1-hydroxybenzotriazole and dicyclohexylcarbodiimide, are reacted with compounds of the general formula III

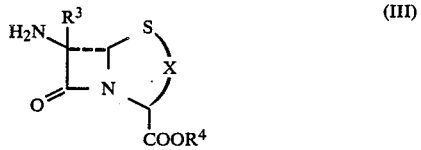

in which $R^3$, $R^4$ and X have the abovementioned meaning, and, if appropriate, protective groups are the split off and the desired salts or, from the salts, the free acids are prepared.

A large number of methods known from cephalosporin or penicillin chemistry can be used for coupling of the aminoacids of the formula II with β-lactams of the formula III.

It has proved advantageous to activate aminoacids of the general formula II and then to couple the products with β-lactams of the general formula III which have been dissolved as salts with an amine. Activation with pivaloyl chloride (IV b) or sulphonic acid derivatives of the formula IVa to give anhydrides of the formula Va and Vb II and 1–1.4 equivalents of an amine are dissolved in a solvent and the solution is reacted with 1 to 1.2 equivalents of a sulphonic acid derivative of the formula IVa or with 1 to 1.2 equivalents of pivaloyl chloride of the formula IVb.

Suitable solvents are all solvents which are stable under the reaction conditions, such as, for example, diethyl ether, tetrahydrofuran, acetonitrile, acetone, methylene chloride, chloroform or dimethylformamide.

Suitable amines are tertiary amines, such as, for example, triethylamine, ethyl diisopropylamine or tributylamine, and also sterically hindered secondary amines, such as, for example, diisopropylamine.

The reactions can be carried out at temperatures between −80° C. and room temperature, preferably between −60° C. and 0° C. The activation is advantageously carried out with Cl—SO$_2$—CH$_3$ in dimethylformamide at −40° C. to −60° C. in the course of 0.2 to 24 hours, preferably 0.5 to 5 hours.

The solvents mentioned for the preparation of the compounds of the formula V can be used to dissolve the compounds of the formula III, and the bases mentioned there can be used as the base.

Activation of the acids of the general formula II by conversion into an activated ester with, for example, N-hydroxysuccinimide and dicyclohexylcarbodiimide or 1-hydroxybenzotriazole and dicyclohexylcarbodiimide is also particularly advantageous.

Suitable solvents are all the solvents which are also suitable for the preparation of anhydrides of the formula V.

The reactions can be carried out at temperatures between −30° C. and +100° C. Advantageously, the

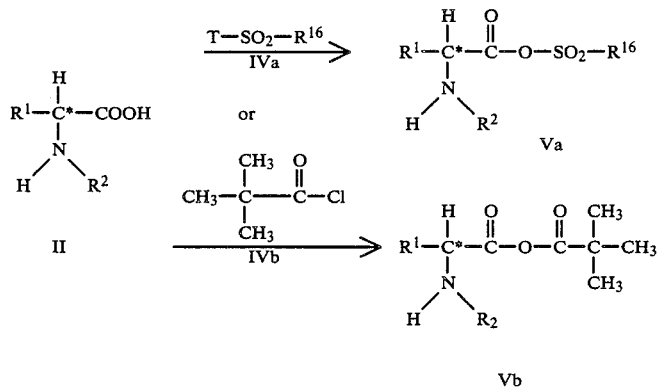

in which $R^1$ has the abovementioned meaning, $R^2$ represents an amino-protective group, T represents a radical $R^{16}SO_2O$ or halogen and $R^{16}$ represents alkyl (C$_1$–C$_{10}$), which is optionally substituted by fluorine, chlorine, cyano, phenyl, C$_1$–C$_4$-alkyl, C$_1$–C$_4$-alkoxy or C$_1$–C$_4$-alkylthio, or represents phenyl which is optionally substituted by fluorine, chlorine, bromine, cyano, C$_1$–C$_4$-alkyl, C$_1$–C$_4$-alkoxy, C$_1$–C$_4$-alkylthio, C$_1$–C$_4$-alkylcarbonyl, nitro, trifluromethyl or phenyl, is particularly advantageous.

If $R^{16}$ is substituted, preferably 1–3 substituents, and preferably those mentioned, are present.

$R^{16}$ especially preferably represents a methyl or p-tolyl radical.

The mixed anhydrides of the formulae Va and Vb are prepared by a process in which the acids of the formula activation is carried out with 1-hydroxybenzotriazole and dicyclohexylcarbodiimide in dimethylformamide at room temperature for 2 to 6 hours, the dicyclohexylurea which has precipitated is filtered off with suction and the product is reacted with a compound of the formula III in the form of a solution of its amine salt in the course of 2 to 24 hours. The solvents mentioned for the preparation of the compounds of the formula V can be used to dissolve the compounds of the formula III, and the amines mentioned there can be used as the base.

Literature for protection of amino and carboxyl and activation of carboxyl: M. Bodanszky, Principles of Peptide Synthesis, Springer-Verlag, 1984. E. Gross, J. Meienhofer, The Peptides Vol. 2, Academic Press, 1980.

The stereochemically uniform D- and L-forms of the compounds of the formula I according to the invention are obtained by separating the diastereomer mixtures, for example on HPLC columns from Merck, Dupont or Whatmann.

On the other hand, the pure D- or L-form (preferably the D-form) is obtained if chemical resolution of the racemate, for example with dehydroabiethylamine, phenylethylamine or camphorsulphonic acid, or resolution of the racemate, for example, via N-acetyl-aminoacid derivatives, for example with subtilisin, penicillin acylase or pig kidney acylase, is already carried out at the stage of the racemic amino acid of the Formula II and the stereochemically uniform D- or L-forms of the compounds of the formula II are then reacted in the manner indicated.

Only some of the compounds of the general formula II are known. The compounds of the formula II can be synthesized by processes which are known from the literature, such as is shown in equation 1, the compounds of the formula VI being the most important key compounds for the new aminoacids of the formula II.

EQUATION 1

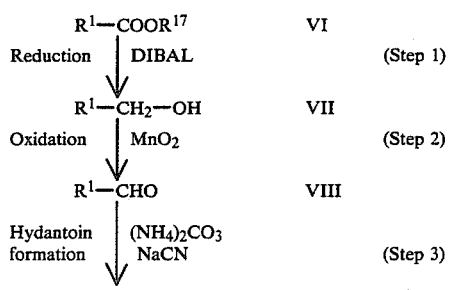

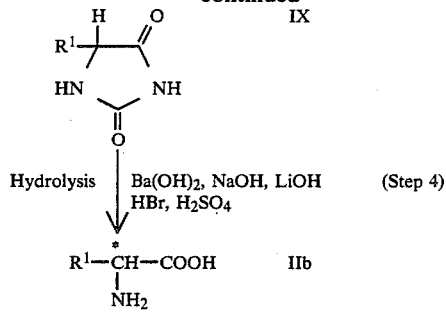

$R^1$ has the abovementioned meaning and $R^{17}$ represents $C_1$–$C_4$-alkyl.

The reduction of esters with diisobutylaluminum hydride (DIBAL) and sodium bis(2-methoxyethoxy)aluminum hydride (Red-Al) to alcohols (step 1) is described in the literature: E. Winterfeld, Synthesis 1975, 617; and A. E. G. Miller et al., J. Org Chem. 24, 627 (1959).

The oxidation of primary alcohols with manganese-(IV) oxide or pyridinium chlorochromate in aldehydes (step 2) is known from the literature: Methoden der Organischen Chemie (Methods of Organic Chemistry), Houben-Weyl, Volume 4/1 b; and G. Piancatelli et al., Synthesis 1982, 245.

The new aminoacids of the formula IIb are obtained by a process in which the aldehydes are reacted with sodium cyanide and ammonium carbonate by processes which are known from the literature [E. Ware, Chemical Reviews 46, 403 (1950)] (step 3) and the products are then hydrolyzed with 10% strength sodium hydroxide solution, 48% strength hydrobromic acid or barium hydroxide or lithium hydroxide solution (step 4).

The preparation of some new aminoacids II and their precursors is described by way of example below, $R^1$–$R^{17}$ having the abovementioned meaning:

(1) Quinolyl-, isoquinolyl- and quinoxalyl-glycines

The starting material for the synthesis of these benzo-fused ring systems are substituted quinoline-, or isoquinoline- and quinoxaline-carboxylic acid derivatives. Substituted quinoxalinecarboxylic acid derivatives are prepared, for example, in accordance with the following synthesis equation:

EQUATION 2

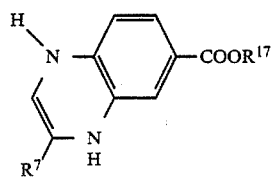 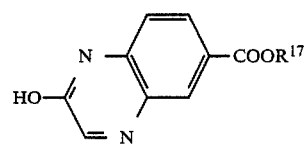

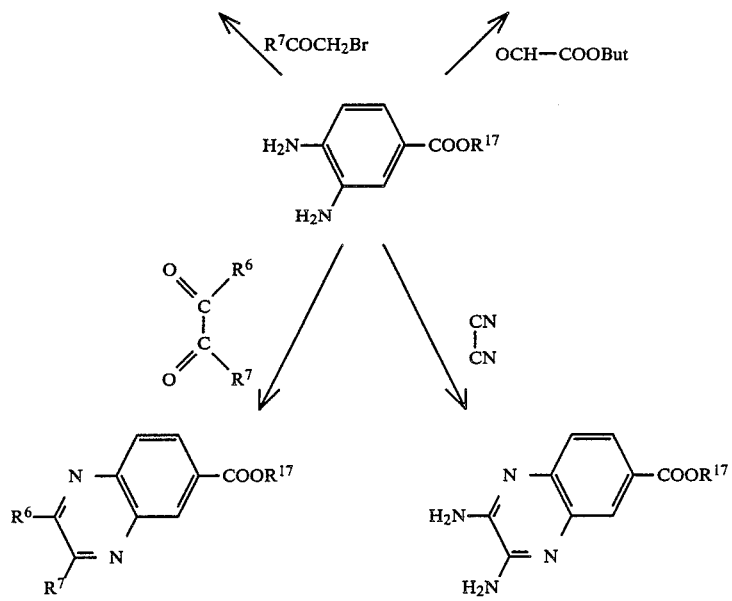

Literature: G. W. H. Cheesman et al., Quinoxaline Chemistry, Advances in Heterocyclic Chemistry, Volume 22, 367, Academic Press (1978).

(2) 1,4-Benzodioxinyl-glycines 3,4-Dihydroxybenzoic acid derivatives are used as the starting material for the synthesis of substituted 1,4-benzodioxinyl-glycines. The new 1,4-benzodioxine-6-carboxylic acid esters are prepared, for example, in accordance with the following synthesis equation:

EQUATION 3

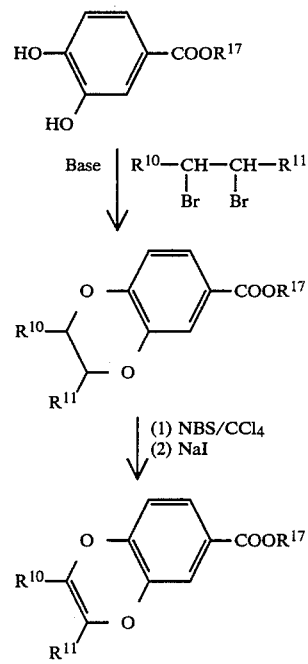

Literature: W. Adam et al., Synthesis 1982, 322

(3) 1,4-Benzoxazinyl-, 1,4-benzothiazinyl- and 1,2,3,4-tetrahydroquinoxalyl-glycines 3-Hydroxy-4-aminobenzoic acid, 3-amino-4-hydroxybenzoic acid, 3-amino-4-mercaptobenzoic acid and 3,4-diamino-benzoic acid in the form of their esters are used as the starting material for the synthesis of these fused phenylglycines. The new benzo-fused carboxylic acid esters are prepared, for example, in accordance with the following synthesis equation:

EQUATION 4

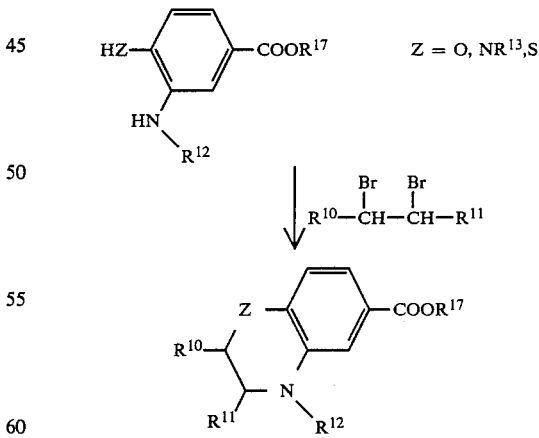

Literature: H. Bartsch et al., J. Heterocyclic Chem. 20, 45 (1983).

(4) Phenoxazinyl- and phenothiazinyl-glycines

Phenoxazine or phenothiazine is the starting material for the synthesis of the phenoxazine- and phenothiazineglycine derivatives

EQUATION 5

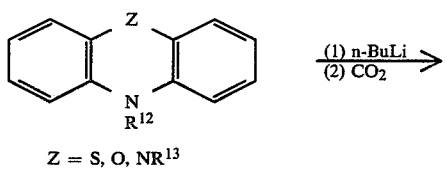

Z = S, O, $NR^{13}$

Literature: M. Ionesen et al., Advances in Heterocyclic Chemistry, Volume 8, 83, Academic Press (1967).

(5) Dibenzopyrrolyl- and dibenzofuryl-glycines

Dibenzofuran and dibenzopyrrole are the starting substances for the synthesis of new fused phenylglycines. The intermediate compounds are prepared, for example, in accordance with the following synthesis equation:

EQUATION 6

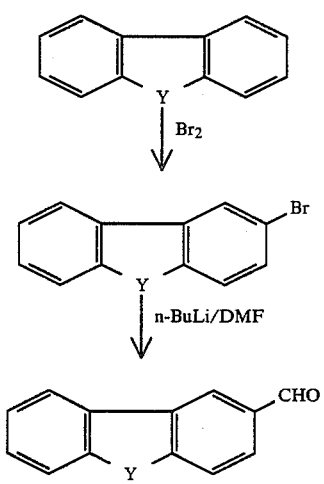

Literature: M. L. Tedjamulia et al., J. Heterocyclic Chem. 20, 861 (1983).

(6) Benzofuryl- and 1,2-benzisoxazolyl-glycines

3-Formyl-4-hydroxy-benzoic acid esters are the starting material for the synthesis of the benzofuryl- and benzisoxazolyl-glycines. The new fused benzoic acid derivatives are prepared, for example, in accordance with the following synthesis equation.

EQUATION 7

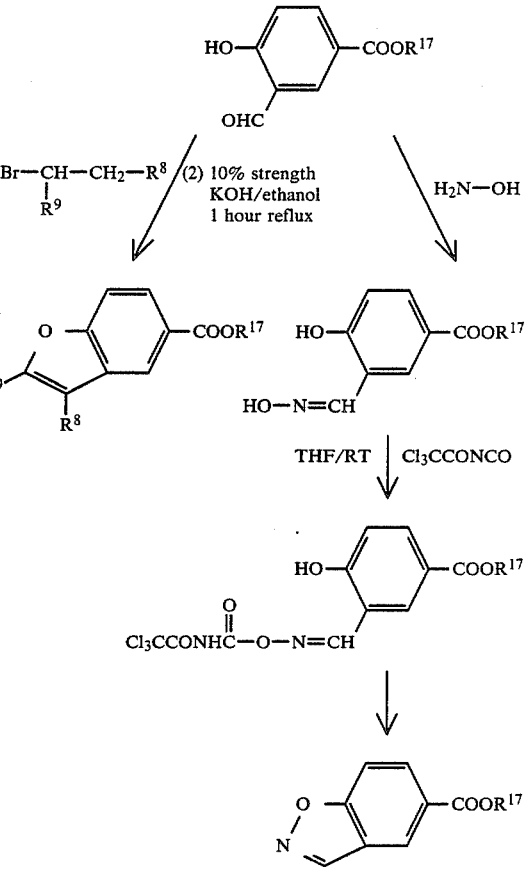

Literature: R. C. Elderfield et al., Benzofuran and its derivatives, Heterocyclic Compounds, Volume 2, 1 (1951). J. Wiley & Sons; P. Cagniant et al., Advances in Heterocyclic Chemistry, Volume 18, Academic Press (1975); and G. Stokker, J. Org. Chem. 48, 2613 (1983).

(7) Indolyl-glycines

3-Methyl-4-nitrobenzoic acid, 2-methyl-3-nitrobenzoic acid and 3-nitro-4-hydrazinobenzoic acid in the form of their esters are used as the starting material for the synthesis of substituted indolylglycines. The substituted indolecarboxylic acid esters are prepared, for example, by the Leimgruber-Batcho and Fischer indole synthesis:

EQUATION 8

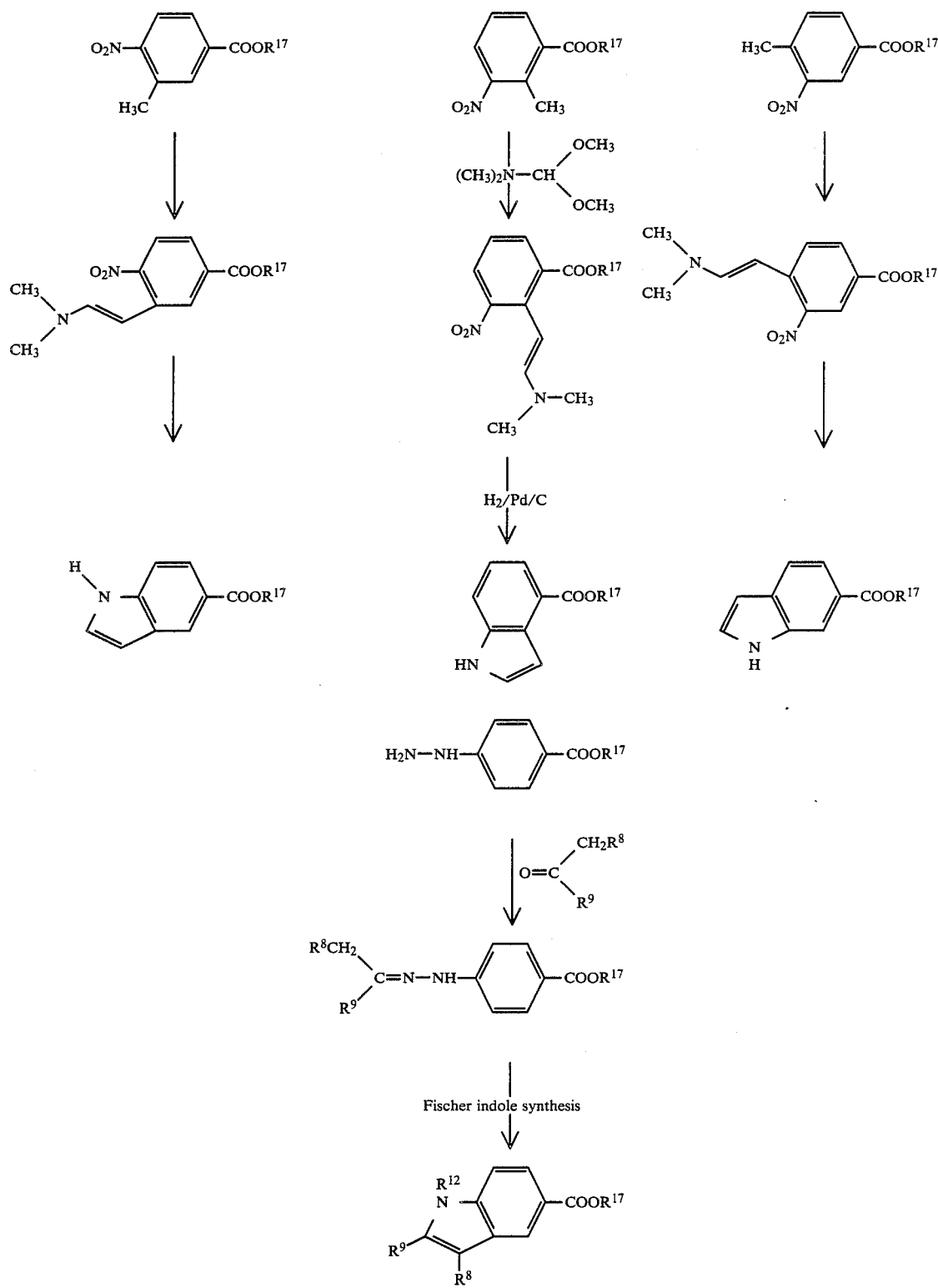
Literature: R. K. Brown, Synthesis of the Indole Nucleus. Heterocyclic Compounds, Part I, 227, J. Wiley & Sons (1972); B. Robinson, Chemical Reviews 63, 373 (1963); and R. D. Clark et al., Heterocycles 22, 195 (1984).
The following penicillin and cephalosporin parent substances are employed for the preparation of the compounds of the formula I according to the invention:

(1) Cephalosporin parent substances (IIIa)

The typical cephalosporin parent substances used here, that is to say 7-amino-3-methyl-3-cephem-4-carboxylic acid (7-ADCA) and 7-amino-3-chloro-3-cephem-4-carboxylic acid (7-ACCA), which are described in J. Med. Chem. 12 (310 C. W. Ryan et al., 1969), U.S. Pat. No. 3,925,372, German Offenlegungsschrift (German Published Specification) DE No. 2,606,196 and U.S. Pat. No. 3,994,884, are represented by the following formula:

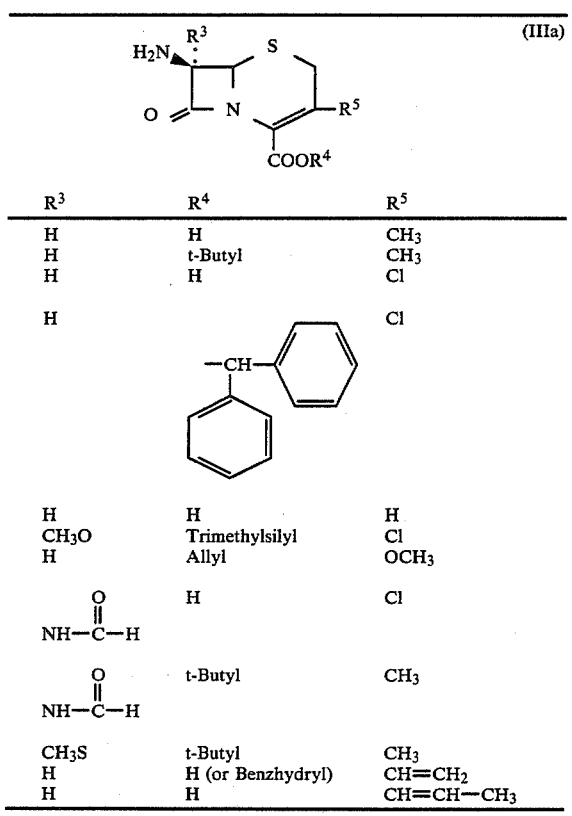

| $R^3$ | $R^4$ | $R^5$ |
|---|---|---|
| H | H | $CH_3$ |
| H | t-Butyl | $CH_3$ |
| H | H | Cl |
| H | —CH(C₆H₅)₂ (benzhydryl) | Cl |
| H | H | H |
| $CH_3O$ | Trimethylsilyl | Cl |
| H | Allyl | $OCH_3$ |
| NH—CO—H | H | Cl |
| NH—CO—H | t-Butyl | $CH_3$ |
| $CH_3S$ | t-Butyl | $CH_3$ |
| H | H (or Benzhydryl) | $CH=CH_2$ |
| H | H | $CH=CH—CH_3$ |

(2) Penicillin parent substances (IIIb)

In addition to 6-amino-penicillanic acid with its typical modifications, 6-aminobisnorpenicillinic acid (British Pat. No. 1,546,622) and 6α-formamidopenicillin (P. H. Milner et al., J. Chem. Soc. Chem. Commun., 1984, (1335)) are used for the preparation of the new compounds of the formula I:

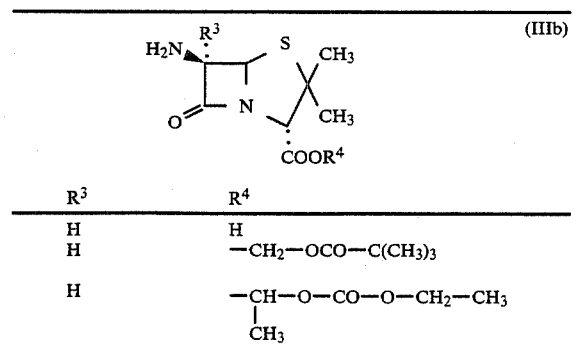

| $R^3$ | $R^4$ |
|---|---|
| H | H |
| H | —CH₂—OCO—C(CH₃)₃ |
| H | —CH(CH₃)—O—CO—O—CH₂—CH₃ |

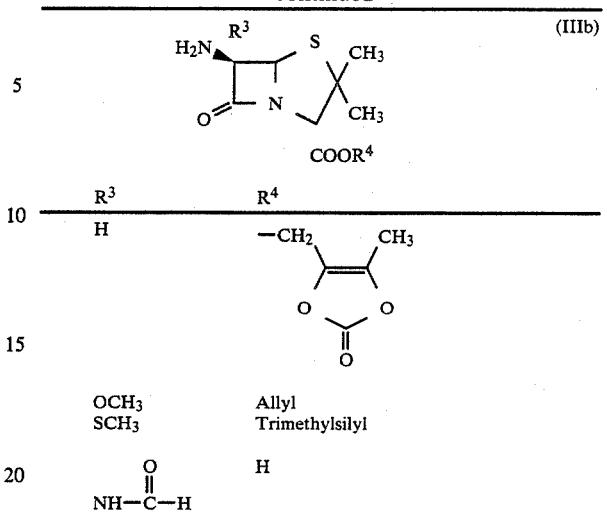

| $R^3$ | $R^4$ |
|---|---|
| H | —CH₂—\[furanonyl methyl\] with CH₃ |
| $OCH_3$ | Allyl |
| $SCH_3$ | Trimethylsilyl |
| NH—CO—H | H |

Especially preferred compounds of the formula I according to the invention are listed in the following tables.

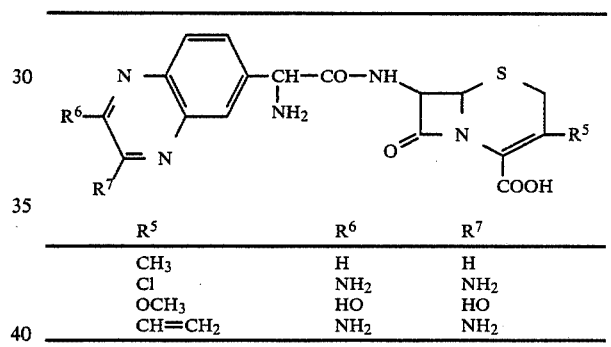

| $R^5$ | $R^6$ | $R^7$ |
|---|---|---|
| $CH_3$ | H | H |
| Cl | $NH_2$ | $NH_2$ |
| $OCH_3$ | HO | HO |
| $CH=CH_2$ | $NH_2$ | $NH_2$ |

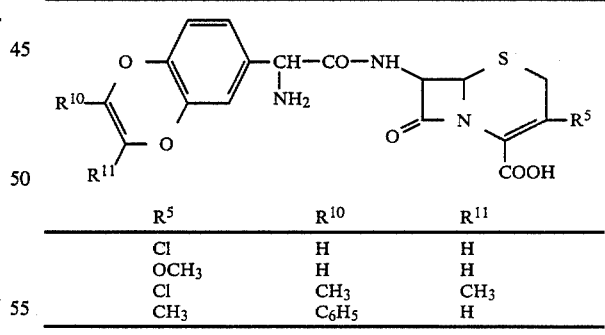

| $R^5$ | $R^{10}$ | $R^{11}$ |
|---|---|---|
| Cl | H | H |
| $OCH_3$ | H | H |
| Cl | $CH_3$ | $CH_3$ |
| $CH_3$ | $C_6H_5$ | H |

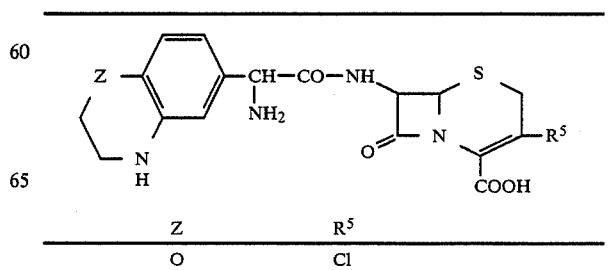

| Z | $R^5$ |
|---|---|
| O | Cl |

-continued

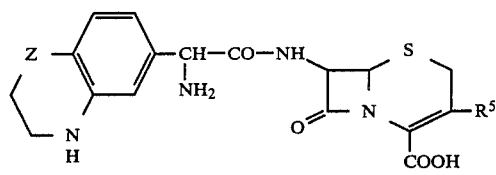

| Z | R⁵ |
|---|---|
| O | CH₃ |
| NH | OCH₃ |
| NH | Cl |
| NH | CH=CH₂ |
| NH | CH=CH—CH₃ |

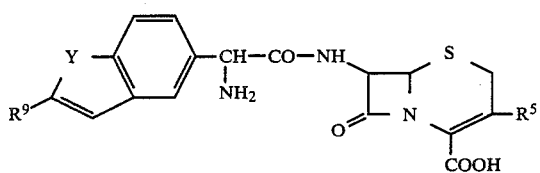

| Y | R⁵ | R⁹ |
|---|---|---|
| NH or O | CH₃ | CH₃ |
| NH or O | Cl | CH₃ |
| NH or O | CH=CH—CH₃ | H |
| NH or O | OCH₃ | 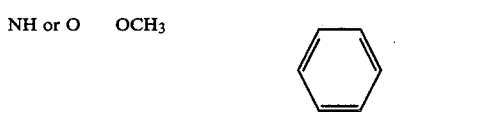 |
| NH or O | Cl |  |
| NH or O | CH₃ | 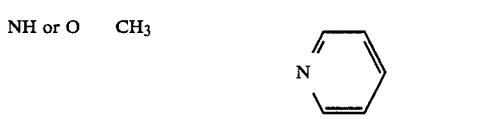 |
| NH or O | Cl |  |
| NH or O | OCH₃ | 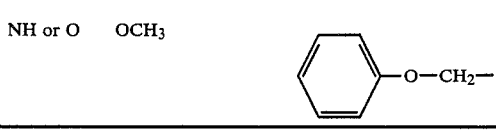 |

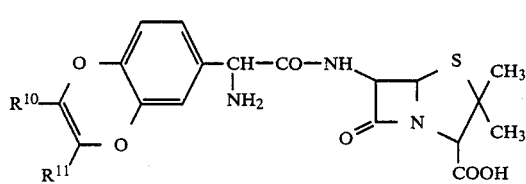

-continued

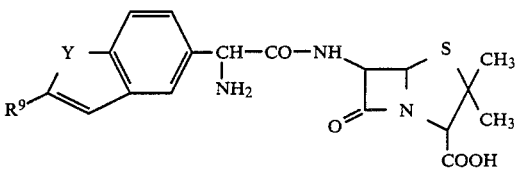

$R^{10}, R^{11}$ = H, CH₃, Phenyl
Y = O, NH
$R^9$ = CH₃, Phenyl, 4-Pyridyl,

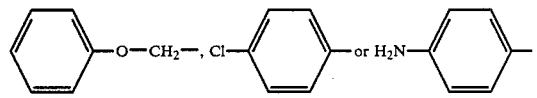

The compounds of the formula I according to the invention have a broad antibacterial spectrum against Gram-positive and Gram-negative germs, in particular against *Staphylococci, Streptococci, Enterococci* and *Haemophilus influenzae*, coupled with a low toxicity.

When administered parenterally or, in particular, orally, the new compounds have a very good action against microorganisms, such as Staphylococci, for example *Staph. aureus* and *Staph. epidermidis*, Streptococci, such as, for example, *Streptococcus pyogenes* and *Streptococcus faecalis*, Enterobacteriaceae, for example *Escherichia coli*, Klebsiella, Salmonella and Shigella, and Proteus, for example *Proteus mirabilis*.

These properties enable them to be used as chemotherapeutic active compounds in human medicine and veterinary medicine. The minimum inhibitory concentrations (MIC values, mg/ml) for Example 7, in comparison with cefaclor, are given in the following table.

The MIC values are determined by the agar dilution test in a solid medium, the reading being obtained after incubation at 37° C. to 18-24 hours. Isosensitest agar is used as the growth medium.

| Germs | Example 7 | Cefaclor |
|---|---|---|
| Staph. 133 | 0.5 | 2 |
| Staph. 25022 | 0.5 | 2 |
| Staph. 25470 | 128 | >128 |
| Staph. E 25185 | 0.125 | 0.5 |
| Strept. faec. 27101 | 64 | >128 |
| Strept. faec. 113 | 32 | >128 |
| Enterococ. 9790 | 16 | 64 |
| Enterococ. 27158 | 8 | 32 |

For example, local and/or systemic diseases which are caused by the abovementioned pathogens or by mixtures thereof can be treated and/or prevented.

Examples which may be mentioned of diseases which can be prevented, alleviated and/or cured by the compounds according to the invention are: diseases of the respiratory tract and of the pharyngeal cavity: otitis and pharyngitis; pneumonia; peritonitis; pyelonephritis; cystitis; and endocarditis, systemic infections, bronchitis, arthritis and local infections.

The present invention includes pharmaceutical formulations which, in addition to non-toxic, inert pharmaceutically suitable excipients, contain one or more compounds according to the invention or consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the active compound content corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, one half, one third or one quarter of a daily dose.

By non-toxic, inert pharmaceutically suitable excipients there are to be understood solid, semi-solid or liquid diluents, fillers and formulation auxiliaries of every kind.

Tablets, dragrees, capsules, pills, granules, suppositories, solutions, suspensions and emulsions, pastes, ointments, gels, creams, lotions, powders and sprays may be mentioned as preferred pharmaceutical formulations.

Tablets, dragrees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) adsorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the compounds listed under (a) to (i).

The tablets, dragrees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, suspending agents, for example ethoxylated isostearyl alcohols, polyoxyethylene sorbitol esters and sorbitan esters, microcrystalline cellulose, aluminum metahydroxide, bentonite, agar-agar and tragacanth, or mixtures of these substances.

The formulation forms mentioned can also contain dyestuffs, preservatives and additives of improved odor and flavor, for example peppermint oil or eucalyptus oil, and sweeteners, for example saccharin.

The therapeutically active compounds should preferably be present in the abovementioned pharmaceutical formulations in a concentration of about 0.1 to 99.5, preferably about 0.5 to 95 percent by weight of the total mixture.

The abovementioned pharmaceutical formulations can also contain other pharmaceutical active compounds in addition to the compounds according to the invention.

The abovementioned pharmaceutical formulations are prepared in the customary manner by known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds according to the invention in total amounts of about 5 to about 1,000, preferably 10 to 200 mg/kg of body weight every 24 hours, if appropriate in the form of several individual doses, to achieve the desired results. An individual dose contains the active compound or compounds according to the invention preferably in amounts of about 1 to about 250, in particular 3 to 60 mg/kg of body weight. However, it may also be necessary to deviate from the dosages mentioned, and in particular to do so as a function of the nature and body weight of the subject to be treated, the nature and severity of the disease, the nature of the formulation and of the administration of the medicament and the period or interval within which administration takes place. Thus, it can in some cases suffice to manage with less than the abovementioned amount of active compound, whilst in other cases the abovementioned amount of active compound must be exceeded. The particular optimum dosage required and the type of administration of the active compounds can easily be determined by anyone skilled in the art on the basis of his expert knowledge.

When used as feed additives, the new compounds can be administered in the customary concentrations and formulations together with the feed or with feed formulations or with the drinking water. It is thereby possible to prevent, alleviate and/or cure an infection by Gram-negative or Gram-positive bacteria and also to achieve promotion in growth and improvement in the utilisation of the feed.

The new compounds are distinguished by powerful antibacterial actions, which have been tested in vivo and in vitro, and by oral absorbability.

For the purpose of extending the action spectrum and in order to achieve an increase in action, especially with bacteria which form β-lactams, the compounds according to the invention can be combined with other antimicrobial active compounds and lactamase inhibitors, for example with penicillins which are particularly penicillinase-resistant and clavulanic acid. Such a combination would be, for example, that with oxacillin or dicloxacillin.

For the purpose of extending the action spectrum and in order to achieve an increase in action, the compounds according to the invention can also be combined with aminoglycoside antibiotics, such as, for example, gentamicin, sisomicin, kanamycin, amikacin or tobramicin.

The invention is illustrated further with the aid of the following examples.

EXAMPLE 1

DL-7-(Quinolyl-6-glycylamido)-3-chloro-3-cephem-4-carboxylic acid

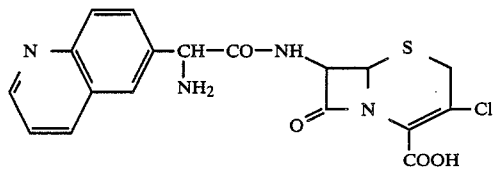

(a) 6-Hydroxymethyl-quinoline (1a)

59.5 g (0.296 mole) of ethyl quinoline-6-carboxylate are stirred in 970 ml of ether at −70° C. with 750 ml (0.9 mole) of diisobutylaluminum hydride (DIBAL, 20% strength in toluene, 1.2 molar) overnight. The temperature is then allowed to rise to −35° C. and 310 ml of sodium chloride solution are added, whereupon the temperature slowly comes to 20° C. The mixture is stirred at 20° C. for 3 hours and the aluminum hydroxide is filtered off with suction and rinsed with ether/ethyl acetate. The organic phase is washed with 100 ml of sodium chloride solution, dried over $Na_2SO_4$ and evaporated. Crude yield: 40 g After chromatography on silica gel (0.04–0.063 mm) with the mobile phase system petroleum ether/ethyl acetate (3:1, 2 l), petroleum ether/ethyl acetate (1:1, 4 l) and petroleum ether/ethyl acetate (1:3, 7–8 l), pure product is obtained.

Yield: 33 g (70%) $C_{10}H_9NO$ (159.2)

NMR (DMSO): δ=4.89 (s, 2H), 5.17 (s, 1H), 7.32 (dd, 1H), 7.62 (dd, 1H), 7.76 (s, 1H), 7.98–8.05 (m, 2H) and 8.75 (dd, 1H) ppm.

(b) Quinoline-6-aldehyde (1b)

32.6 g (0.205 mole) of 1a are stirred in 1,220 ml of methylene chloride with 122 g (1.4 moles) of manganese(IV) oxide for 3 days, the oxidizing agent is filtered off with suction and the filtrate is concentrated to dryness.

Yield: 26 g (81%); $C_{10}H_7NO$ (157.2).

NMR (DMSO): δ=7.74 (dd, 1H), 8.2 (s, 2H), 8.64 (dd, 1H), 8.68 (s, 1H), 9.12 (d, 1H) and 10.25 (s, 1H) ppm. (c) 5-(Quinol-6-yl)-2,4-imidazolidinedione (1c).

26 g (0.165 mole) of 1b, dissolved in 165 ml of ethanol, are added dropwise to a solution of 12.2 g (0.248 mole) of sodium cyanide and 63.5 g (0.662 mole) of ammonium carbonate in 165 ml of water and the mixture is stirred at 60° C. for 22 hours. After the ethanol has been distilled off in vacuo, the residual solution is acidified to pH 2 at 0° C. with 2N hydrochloric acid and then brought back to pH 4.5 with 2N sodium hydroxide solution and the hydantoin which has precipitated is filtered off with suction.

Yield: 27 g (76%); $C_{12}H_9N_2O_2$ (213.2).

NMR (DMSO): δ=5.44 (s, 1H), 7.58 (dd, 1H), 7.75 (dd, 1H), 8.0 (s, 1H), 8.1 (d, 1H), 8.45 (dd, 1H), 8.6 (s, 1H), 8.95 (d, 1H) and 10.85 (broad s, 1H) ppm.

(d) DL-α-Amino-α-(quinol-6-yl) acetic acid (1d)

27 g (0.127 mole) of 1c and 144.2 g (0.457 mole) of barium hydroxide in 1,200 ml of $H_2O$ are stirred at 100° C. for 24 hours. The suspension is then diluted with 500 ml of water, $CO_2$ is passed in at 100° C. for 2 hours and the barium carbonate is filtered off with suction and rinsed with boiling water. The filtrate is concentrated to dryness.

Yield: 16.6 g.

Very dilute sulphuric acid is added to the residue in boiling water, the product which has precipitated is filtered off and the filtrate is lyophilized.

Yield: 12.1 g (38%) $C_{11}H_{10}N_2O_2 \cdot \frac{1}{2}H_2SO_4$ (251.2).

| calculated: | C 52.58 | H 4.41 | N 11.4 | S 6.38 |
| found: | C 51.1 | H 4.7 | N 10.9 | S 5.4 |

NMR (DCOOD): δ=5.88 (s, 1H), 8.36 (t, 1H), 8.48 (d, 1H), 8.62 (d, 1H), 8.74 (s, 1H) and 9.4–9.48 (m, 2H) ppm.

(e) DL-α-(t-Butyloxycarbonylamino-α-quinol-6-yl) acetic acid (1e)

16.6 g (0.066 mole) of 1d are dissolved in 166 ml of 2N sodium hydroxide solution, 166 ml of $H_2O$ and 338 ml of dioxane, 43.2 g (0.198 mole) of di-t-butyl dicarbonate are added dropwise in the course of 30 minutes and the mixture is stirred at room temperature for 30 hours. The dioxane is distilled off, the residual solution is washed with ethyl acetate/petroleum ether (1:1) and the aqueous phase is acidified to pH 2 with 2N HCl, while cooling with ice. The mixture is extracted twice with ethyl acetate and the organic phase is washed with sodium chloride solution, dried over $Na_2SO_4$ and concentrated to dryness.

Yield: 10.2 g (51%); $C_{16}H_{18}N_2O_4$ (302.3).

(f) DL-7-(Quinol-6-ylglycylamido)-3-chloro-3-cephem-4-carboxylic acid (1f)

Activation of the precursor acid 2.4 g (7.93 mmol) of 1e are dissolved in 30 ml of dimethylformamide, 1.11 ml (7.93 mmol) of triethylamine are added, 0.977 ml (7.93 mmol) of pivaloyl chloride is injected in dropwise at −40° C. and the mixture is stirred at −30° C. to −15° C. for 3 hours.

Preparation of the amine component 1.87 g (7.97 mmol) of 7-amino-3-chloro-3-cephem-4-carboxylic acid (7-ACCA) are suspended in 15 ml of tetrahydrofuran and 7 ml of H$_2$O, and are dissolved with a 10% strength solution of triethylamine in tetrahydrofuran (pH 8.3). 2 ml of dimethylformamide are then added to obtain a uniform phase.

Coupling and isolation

The 7-ACCA solution is injected, at −40° C., into the anhydride formed and the mixture is then stirred, without a low temperature bath. After 1 hour, 5–10 ml of H$_2$O are added and the pH is brought to 7.3 with 10% strength triethylamine in tetrahydrofuran. After a further 2 hours, about 140 ml of H$_2$O are added, ethyl acetate is added, with stirring, and the mixture is acidified to pH 1.7 at 0° C. The organic layer is separated off, washed with sodium chloride and dried with Na$_2$SO$_4$ and the solvent is distilled off in vacuo.

The residue is dissolved in a little tetrahydrofuran and the solution is stirred into petroleum ether.

Yield: 2.6 g (63%); C$_{23}$H$_{23}$ClN$_4$O$_6$S (519.0).

2.5 g (4.82 mmol) of Boc-protected cephalosporin are dissolved in 25 ml of methylene chloride, 0.5 ml of anisole and 25 ml of trifluoroacetic acid (TFA) are added at 0° C. and the mixture is stirred for 15 minutes, without cooling. The solution is then concentrated to dryness in vacuo and ether is added to the residue. The trifluoroacetate is filtered off with suction, washed with ether and dried in vacuo. To remove the trifluoroacetic acid, the substance is dissolved in 200 ml of H$_2$O and the solution is introduced onto a column filled with Amberlite IRA-68 (acetate form). The column is rinsed with 150 ml of water and the entire eluate is lyophilized.

Yield: 1.2 g (57%); C$_{18}$H$_{15}$ClN$_4$O$_4$S.H$_2$O (436.9).

NMR (DCOOD): δ=3.45–4.0 (mm, 2H), 5.28–5.38 (dd, 1H), 5.84–5.89 (dd, 1H), 5.98 (d, 1H), 8.35 (m, 1H), 8.46. (m, 1H), 8.58 (d, 1H), 8.76 (s, 1H) and 9.38–9.48 (m, 2H) ppm.

EXAMPLE 2

DL-7-(Quinol-6-ylglycylamido)-3-methyl-3-cephem-4-carboxylic acid

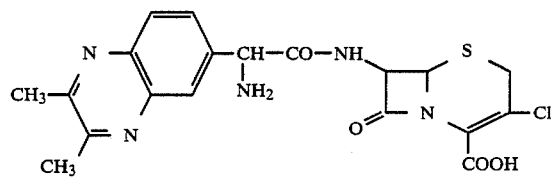

3.02 g (10 mmol) of 1e and 1.53 g (10 mmol) of 1-hydroxybenzotriazole are dissolved in 15 ml of tetrahydrofuran, under nitrogen. 2.06 g (10 mmol) of N,N'-dicyclohexylcarbodiimide (DCC), dissolved in 10 ml of tetrahydrofuran, are added at 10° C. The mixture is stirred at room temperature for 2 hours, 2.7 g (10 mmol) of t-butyl 7-amino-3-methyl-3-cephem-4-carboxylate, dissolved in 10 ml of CH$_2$Cl$_2$, are added to the solution of the activated ester at 0° C. and the mixture is then stirred overnight, without cooling. The urea which has precipitated is filtered off with suction and washed with tetrahydrofuran and the filtrate is concentrated to dryness. The residue is dissolved in ethyl acetate, the solution is washed with NaHCO$_3$ solution and water and dried over Na$_2$SO$_4$ and the filtrate is concentrated to dryness in vacuo.

Yield: 1.9 g (34%); C$_{28}$H$_{34}$N$_4$O$_6$S (554.7).

1.7 g (3.06 mmol) of Boc-protected cephalosporin are dissolved in 30 ml of CH$_2$Cl$_2$, 0.5 ml of anisole and 30 ml of TFA are added at 0° C. and the mixture is stirred at room temperature for 1 hour. The solvent is then distilled off in vacuo and the oily residue is triturated with ether. The trifluoroacetate is filtered off with suction, washed with ether, dried and then dissolved in 200 ml of H$_2$O and the solution is introduced onto a column containing Amberlite IRA-68 (acetate form). The column is rinsed with 100 ml of water and the entire eluate is lyophilized.

Yield: 0.8 g (63%); C$_{19}$H$_{18}$N$_4$O$_4$S.H$_2$O (416.4).

NMR (DCOOD): δ=2.17 (d, 3H), 3.18–3.6 (m, 2H), 5.18–5.27 (dd, 1H), 5.86–6.02 (dd and s, 2H), 8.34 (m, 1H), 8.47 (d, 1H), 8.60 (t, 1H), 8.77 (s, 1H) and 9.38–9.48 (m, 2H) ppm.

EXAMPLE 3

DL-7-(2,3-Dimethylquinoxaline-6-glycylamido)-3-chloro-3-cephem-4-carboxylic acid

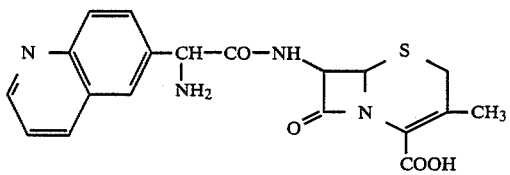

(a) Methyl 2,3-dimethylquinoxaline-6-carboxylate (3a)

55.8 g (0.354 mole) of methyl 3,4-diaminobenzoate and 30.5 g (0.354 mole) of diacetyl are heated under reflux in 500 ml of toluene for 3 hours, using a water separator. The toluene is distilled off in vacuo and the residue is dissolved in ethyl acetate under the influence of heat, active charcoal being added, the active charcoal is separated off via a Seitz filter and the filtrate is concentrated to dryness.

Yield: 72.6 g (95%); C$_{12}$H$_{12}$N$_2$O$_2$ (216.2).

NMR (DMSO): δ=2.7 (s, 6H), 3.96 (s, 3H), 9.0 (d, 1H), 9.13 (d, 1H) and 9.42 (s, 1H) ppm.

(b) 2,3-Dimethyl-6-hydroxymethyl-quinoxaline (3b)

72.6 g (0.336 mole) of 3a are reduced analogously to Example 1a with 672 ml of DIBAL (25% strength solution in toluene) in 1,100 ml of tetrahydrofuran at −70° C. to give the quinoxaline alcohol.

Yield: 56.8 g (90%); C$_{11}$H$_{12}$N$_2$O (188.2).

NMR (DMSO): δ=2.6 (s, 6H), 4.67 (d, 2H), 5.45 (t, 1H), 7.62 (dd, 1H) and 7.81–7.89 (s and d, 2H) ppm.

(c) 2,3-Dimethylquinoxaline-6-carboxaldehyde (3c)

56.8 g (0.302 mole) of 3b are stirred analogously to Example 1b with 160 g (1.84 moles) of manganese(IV) oxide in 1,000 ml of CH$_2$Cl$_2$ at room temperature for 4 days.

Crude yield: 54 g.

After chromatography on silica gel with the mobile phase system toluene/ethyl acetate (1:1), 36 g (64%) of pure material are obtained.

C$_{11}$H$_{10}$N$_2$O (186.2).

NMR (DMSO): δ=2.75 (s, 6H), 8.13 (d, 1H), 8.69 (s, 1H) and 10.27 (s, 1H) ppm.

(d)
5-(2,3-Dimethylquinoxalin-6-yl)-4-imidazolidinedione (3d)

36 g (0.193 mole) of 3c are reacted analogously to Example 1c with 77.9 g (0.813 mole, 4.2 equivalents) of ammonium carbonate and 14.7 g (0.230 mole, 1.55 equivalents) of sodium cyanide in methanol/ethanol/water.

Yield: 42.2 g (85%); $C_{13}H_{12}N_4O_2$(256.3).

NMR (DMS): $\delta$=2.66 (s, 6H), 5.48 (s, 1H), 7.72 (dd, 1H), 7.9 (s, 1H), 8.02 (d, 1H), 8.66 (s, 1H) and 10.98 (broad s, 1H) ppm.

(e)
DL-α-t-Butyloxycarbonylamino-α-(2,3-dimethyl-quinoxalin-6-yl) acetic acid (3e)

39.7 g (0.155 mole) of 3d are heated at 100° C. with 37.1 g (1.55 moles) of lithium hydroxide in 1,000 ml of water for 24 hours. The solution is filtered hot, the residue on the filter is rinsed with hot water and the filtrate is acidified to pH 2 at 0° C. with hydrochloric acid. The solution is brought back to pH 4.5 by means of 2N sodium hydroxide solution and is concentrated to dryness in vacuo. 2.5 g (10.8 mmol) of 2,3-dimethyl-quinoxaline-6-glycine are reacted with 4.7 g (21.6 mmol) of di-t-butyl dicarbonate in 10% strength NaHCO$_3$ solution (50 ml) and 50 ml of dioxane and the mixture is worked up analogously to Example 1e.

Yield: 1.8 g (50%, tetrahydrofuran/petroleum ether); $C_{17}H_{21}N_3O_4$ (331.4).

NMR (DMSO): $\delta$=1.42 (s, 9H), 2.7 (s, 6H), 5.42 (d, 1H), 7.8 (d, 1H), 7.88 (d, 1H) and 7.95–8.02 (s and d, 2H) ppm.

(f)
DL-7-(2,3-Dimethylquinoxaline-6-glycylamido)-3-chloro-Δ²/Δ³-cephem-4-carboxylic acid (3f)

1.05 ml (6.03 mmol) of ethyldiisopropylamine and 0.467 ml (6.03 mmol) of methanesulphonyl chloride are slowly injected in succession into a solution, cooled to −50° C., of 2.0 g (6.03 mmol) of 3e in 15 ml of dimethylformamide and 15 ml of tetrahydrofuran. The mixture is stirred at −50° C. for 45 minutes and a solution (0° C.) of 2.54 g (6.33 moles) of diphenylmethyl 7-amino-3-chloro-3-cephem-4-carboxylate and 1.1 ml (6.33 mmol) of ethyldiisopropylamine in 12 ml of tetrahydrofuran and 12 ml of CH$_2$Cl$_2$ is added dropwise. The mixture is subsequently stirred at −50° C. for 15 minutes and then for a further 45–60 minutes without cooling. Thereafter, the solvent is distilled off in vacuo, the residue is dissolved in 300 ml of ethyl acetate and the solution is washed with 0.1N hydrochloric acid, sodium chloride solution, NaHCO$_3$ solution and water. After drying and distilling off the ethyl acetate, 3.5 g (81%) of crude product are obtained, and are dissolved in 100 ml of ethyl acetate, with the addition of silica gel, the solution then being concentrated in vacuo. The powder is introduced onto a column (100 g of silica gel, 0.04–0.063 mm) and the column is eluted with toluene/ethyl acetate (4:1) and toluene/ethyl acetate (3:1) in succession.

Yield: 1.7 g (40%)

1.6 g of Boc-protected cephalosporin are deblocked analogously to Example 2. The trifluoroacetate is converted into the betaine with Amberlite IRA-68 (acetate form).

Yield: 0.45 g (42%); $C_{19}H_{18}ClN_5O_4S.2H_2O$ (483.9).

The 4 isomeric cephalosporins are separated by preparative HPLC (Hibar 250-25, RP-18, 7 μm) with the mobile phase 0.1% strength trifluoroacetic acid-methanol (80:20).

D-Form (peak III)

NMR (DCOOD): $\delta$=3.16 (d, 6H), 3.52 (d, 1H), 3.86 (d, 1H), 5.31 (d, 1H), 5.97 (d, 1H), 6.02 (s, 1H), 8.4 (s, 1H) 8.56 (d, 1H) and 8.71 (s, 1H) ppm.

EXAMPLE 4
DL-7-(Indol-4-ylglycylamido)-3-chloro-3-cephem-4-carboxylic acid

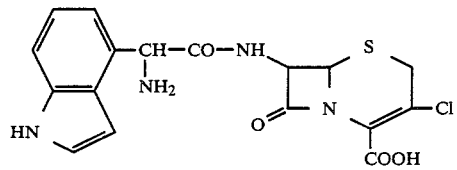

(a) 5-(Indolyl-4-yl)-2,4-imidazolidinedione (4a)

7.8 g (53.7 mmol) of indole-4-carboxaldehyde are reacted analogously to Example 1c with 4.05 g (82.7 mmol) of sodium cyanide and 14.0 g (146 mmol) of ammonium carbonate in ethanol and water.

Yield: 6.4 g (55%); $C_{11}H_9N_3O_2$ (215.2).

|  |  |  |  |
|---|---|---|---|
| calculated: | C 61.4 | H 4.2 | N 19.5 |
| found: | C 60.4 | H 4.3 | N 19.7 |

(b) DL-α-Amino-α-indol-4-yl) acetic acid (4b)

68.0 g (0.316 mole) of 4a are stirred analogously to Example 1d with 365.5 g (1.152 moles) of barium hydroxide in 2,200 ml of H$_2$O at 100° C. for 24 hours.

Yield: 40 g (56%); $C_{10}H_{10}N_2O_2.2H_2O$ (226.2).

|  |  |  |  |
|---|---|---|---|
| calculated: | C 53.10 | H 6.24 | N 12.39 |
| found: | C 53.7 | H 5.7 | N 12.1 |

NMR (DMSO): $\delta$=4.6 (s, 1H), 6.64 (s, 1H), 7.02 (d, 2H), 7.32–7.38 (dd, 2H), 7.7–8.1 (broad s, 1H) and 11.33 (s, 1H) ppm.

(c) DL-α-(t-Butyloxycarbonylamino-α-indol-4-yl) acetic acid (4c)

6.0 g (26.5 mmol) of 4b are reacted analogously to Example 1e with 11.5 g (53 mmol) of di-t-butyl dicarbonate in dioxane, water and 2N sodium hydroxide solution.

Yield: 5.2 g (68%); $C_{15}H_{18}N_2O_4$ (290.3).

NMR (DMSO): $\delta$=1.37 (s, 9H), 5.5 (d, 1H), 6.54 (s, 1H), 6.98–7.1 (m, 2H), 7.37 (m, 2H) and 11.18 (s, 1H) ppm.

(d)
DL-7-[2-(t-Butyloxycarbonylamino)-indol-4-ylglycylamido]-3-chloro-3-cephem-4-carboxylic acid (4d)

3.4 ml (24.3 mmol) of triethylamine and 2 drops of N-methylmorpholine are added to 7.05 g (24.3 mmol) of 4c in 50 ml of tetrahydrofuran and 20 ml of dimethylformamide, and 3.15 ml (24.3 mmol) of isobutyl chloroformate are added at −30° C. After 60 minutes at −30° C. to −10° C., a precooled triethylamine solution of 6.55 g (27.9 mmol) of 7-ACCA in tetrahydrofuran/water (3:1) is added. The mixture is subsequently stirred for 90 minutes, without cooling, and the pH value is brought to 7.2. Ethyl acetate/water are added and the mixture is acidified to pH 2 at 0° C. The ethyl acetate phase is separated off, washed, dried over $Na_2SO_4$ and concentrated to 40 ml and the concentrate is stirred into petroleum ether. The product which has precipitated is filtered off with suction and dried.

Yield: 9.8 g (80%); $C_{22}H_{23}ClN_4O_6S$ (506.9).

NMR (DMSO): δ=1.4 (s, 9H), 3.6–4.04 (mm, 2H), 5.18–5.26 (dd, 2H), 5.72 (d, 1H), 5.81–5.88 (dd, 1H), 6.64 (s, 1H), 7.04 (m, 2H), 7.38 (m, 2H), 9.22 (t, 1H) and 11.18 (d, 1H) ppm.

(e) DL-7-(Indol-4-ylglycylamido)-3-chloro-3-cephem-4-carboxylic acid (4e)

10 g (19.7 mmol) of 4d are stirred with 50 ml of TFA at 10° C. without the addition of anisole for 15 minutes. The trifluoroacetate is isolated as the betaine analogously to Example 1f.

Yield: 4.2 g (48%); $C_{17}H_{15}ClN_4O_4S \cdot 2H_2O$ (442.9).

NMR (DCOOD): δ=3.43–3.95 (mm, 2H), 5.23–5.32 (dd, 1H), 5.85–5.94 (dd and d, 2H), 7.27 (m, 3H), 7.5 (s, 1H) and 7.68 (m, 1H) ppm.

EXAMPLE 5

D-7-(Indol-4-ylglycylamido)-3-chloro-3-cephem-4-carboxylic acid (5a) and L-form (5b)

The diastereomer mixture 4e is resolved into the D- and L-form on a preparative Merck column (Hibar 250-25, RP-18, 7 μm, mobile phase: 0.1% strength trifluoroacetic acid-methanol (85:15), 220 nm).

(a) D-Form (peak II)

NMR (DCOOD): δ=3.5 (d, J=18 Hz, 1H), 3.84 (d, J=18 Hz, 1H), 5.25 (d, J=5 Hz, 1H), 5.89 (s, 1H), 5.93 (d, J=5 Hz, 1H), 7.3 (d, 3H), 7.52 (s, 1H) and 7.68 (t, 1H) ppm.

(b) L-Form (peak I)

NMR (DCOOD): δ=3.72 (d, J=18 Hz, 1H), 3.95 (d, J=18 Hz, 1H), 5.33 (d, J=5 Hz, 1H), 5.88 (d, J=5 Hz, 1H), 5.91 (s, 1H), 7.3 (m, 3H), 7.52 (s, 1H) and 7.68 (m, 1H) ppm.

EXAMPLE 6

DL-7-(Indol-5-ylglycylamido)-3-chloro-3-cephem-4-carboxylic acid

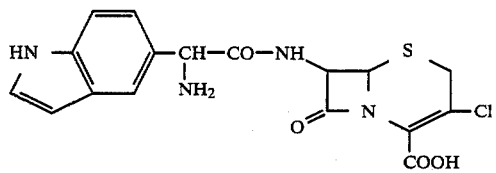

(a) Methyl trans-3-[β-(dimethylamino)vinyl]-4-nitrobenzoate (6a)

A solution of 86.4 g (0.443 mole) of methyl 3-methyl-4-nitrobenzoate and 158.2 g (1.329 moles) of N,N-dimethylformamide dimethyl acetal in 500 ml of dimethylformamide is heated at 130° C. for 6 hours. The dimethylformamide is then distilled off under a high vacuum and the residue is dried at 20° C. in vacuo.

Crude yield: 100.3 g (91%); $C_{12}H_{14}N_2O_4$ (250.3).

NMR (DMSO): δ=2.96 (s, 6H), 3.96 (s, 3H), 5.8 (d, J=14 Hz, 1H), 7.1 (d, J=14 Hz, 1H), 7.57 (dd, 1H), 7.85 (d, J=8.5 Hz, 1H) and 8.15 (s, 1H) ppm.

(b) Methyl indole-5-carboxylate (6b)

227 g (1.106 moles) of 6a (crude product) are hydrogenated with 55 g of palladium on active charcoal (10% Pd) under 10 bar in the presence of hydrogen in 2,000 ml of toluene for 4 hours. After the catalyst has been separated off and the toluene solution has been concentrated, the indole derivative is chromatographed on silica gel (2,300 g, 0.04–0.063 mm) using the eluting agent petroleum ether/ethyl acetate (4:1) and petroleum ether/ethyl acetate (3:1).

Yield: 58.9 g (30%); $C_{10}H_9NO_2$ (175.2).

NMR (CDCl$_3$): δ=3.94 (s, 3H), 6.62 (s, 1H), 7.24 (t, 1H), 7.38 (d, 1H), 7.9 (d, 1H), 8.41 (s, 1H) and 8.68 (broad s, 1H) ppm.

(c) Indole-5-methanol (6c)

96 g (0.548 mole) of 6b are treated analogously to Example 1a in 1,800 ml of ether and 1,391 ml (1.67 moles) of DIBAL (1.2 molar in toluene). After chromatography on silica gel with gradient elution with petroleum ether/ethyl acetate (3:1) and petroleum ether/ethyl acetate (1:1), 39.3 g (49%) of pure product are obtained. $C_9H_9NO$ (147.2)

NMR (CDCl$_3$): δ=3.91 (broad s, 1H), 4.72 (s, 2H), 6.45 (m, 1H), 7.17 (m, 2H), 7.37 (d, 1H), 7.6 (s, 1H) and 9.88 (broad s, 1H) ppm.

(d) Indole-5-carboxaldehyde (6d)

51.1 g (0.347 mole) of 6c are stirred analogously to Example 1b in 1,900 ml of $CH_2Cl_2$ and 200 ml of tetrahydrofuran with 190 g (2.18 moles) of manganese(IV) oxide at 20° C. overnight.

Yield: 44.3 g (85%); $C_9H_7NO$ (145.2).

NMR (CDCl$_3$): δ=6.71 (dd, 1H), 7.34 (dd, 1H), 7.5 (d, 1H), 7.79 (dd, 1H), 8.2 (d, 1H), 8.93 (broad s, 1H) and 10.04 (s, 1H) ppm.

(e) 5-(Indol-5-yl)-2,4-imidazolidinedione (6e)

14.5 g (0.1 mole) of 6d are stirred analogously to Example 1c in ethanol and water with 7.35 g (0.15 mole) of sodium cyanide and 38.4 g (0.4 mole) of ammonium carbonate at 60° C. for 2 days.

Yield: 17.3 g (81%); $C_{11}H_9N_3O_2$ (215.2).

(f) DL-α-Amino-α-(indol-5-yl) acetic acid (6f)

17.3 g (0.08 mole) of 6e are stirred analogously to Example 1d with 92.12 g (0.292 mole) of barium hydroxide in 560 ml of water at 100° C. for 24 hours.

Yield: 12.1 g (67%); $C_{10}H_{10}N_2O_2 \cdot 2H_2O$ (226.2).

| calculated: | C 53.10 | H 6.24 | N 12.39 |
| --- | --- | --- | --- |
| found: | C 54.8 | H 5.0 | N 12.4 |

NMR (NaOD): δ=4.43 (s, 1H), 6.57 (d, 1H), 7.22 (d, 1H), 7.39 (d, 1H), 7.5 (d, 1H) and 7.65 (s, 1H) ppm.

(g) DL-α-(t-Butyloxycarbonylamino-α-indol-5-yl) acetic acid (6g)

14.0 g (0.0736 mole) of 6f are stirred analogously to Example 1e with 64.2 g (0.294 mole) of di-t-butyl dicarbonate in dioxane, water and 2N sodium hydroxide solution at room temperature for 30 hours.

Yield: 13.1 g (73%); $C_{15}H_{18}N_2O_4$ (290.3).

NMR (DMSO): $\delta = 1.38$ (s, 9H), 5.1 (d, 1H), 6.41 (s, 1H), 7.1 (dd, 1H), 7.34 (dd, 1H), 7.4 (d, 1H), 7.55 (s, 1H), 11.1 (s, 1H) and 12.52 (broad s, 1H) ppm.

(h) DL-7-(Indol-5-ylglycylamido)-3-chloro-3-cephem-4-carboxylic acid (6h)

3.5 g (12.1 mmol) of 6g are reacted analogously to Example 4d with 1.69 ml (12.1 mmol) of triethylamine, 2 drops of N-methylmorpholine, 1.57 ml (12.1 mmole) of isobutyl chloroformate and 2.84 g (12.1 mmol) of 7-ACCA in 20 ml of tetrahydrofuran and 20 ml of dimethylformamide.

Yield: 4.6 g (75%); $C_{22}H_{23}ClN_4O_6S$ (506.9).

4 g (7.89 moles) of Boc-protected cephalosporin are stirred in 40 ml of $CH_2Cl_2$, 40 ml of TFA and 10 ml of thioanisole at 0° C. under argon for 10 minutes. The trifluoroacetic acid is removed and the betaine is formed analogously to Example 1g.

Yield: 1 g (29%); $C_{17}H_{15}ClN_4O_4S.2H_2O$ (442.9).

NMR (DCOOD): $\delta = 3.5-4.02$ (mm, 2H), 5.28–5.4 (dd, 1H), 5.65–5.92 (mm, 2H), 7.27 (m, 2H), 7.37 (m, 2H) and 7.68 (m, 1H) ppm.

EXAMPLE 7

DL-7-(Benzofur-5-ylglycylamido)-3-chloro-3-cephem-4-carboxylic acid

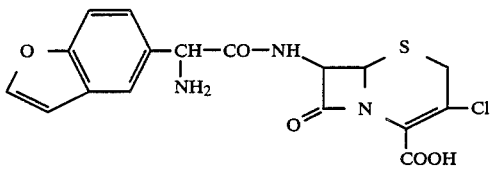

(a) 5-Hydroxymethyl-benzofuran (7a)

5.8 g (32.9 mmol) of methyl benzofuran-5-carboxylate are stirred analogously to Example 1 g in 50 ml of tetrahydrofuran with 64.5 ml (98.6 mmol) of DIBAL (1.53 molar) at −70° C. overnight.

Yield: 3.9 g (80%); $C_9H_8O_2$ (148.2).

NMR (DMSO): $\delta = 4.6$ (d, 2H), 5.24 (t, 1H), 6.96 (d, 1H), 7.3 (dd, 1H), 7.58 (d, 1H), 7.62 (s, 1H) and 7.99 (d, 1H) ppm.

(b) Benzofurany-5-carboxaldehyde (7b)

5.3 g (35.8 mmol) of 7a are stirred analogously to Example 1b in 360 ml of methylene chloride with 19.7 g (227 mmol) of manganese(IV) oxide at room temperature for 2 days.

Yield: 4.6 g (88%); $C_9H_6O_2$ (146.1).

NMR (DMSO): $\delta = 7.21$ (d, 1H), 7.84 (d, 1H), 7.96 (dd, 1H), 8.22 (d, 1H), 8.32 (s, 1H) and 10.12 (s, 1H) ppm.

(c) DL-α-Amino-α-(benzofur-5-yl)-acetic acid (7c)

19.0 g (0.13 mole) of 7b are stirred analogously to Example 1c in ethanol and water with 9.6 g (0.195 mole) of sodium cyanide and 49.9 g (0.52 mole) of ammonium carbonate at 60° C. for 18 hours.

Yield: 21.3 g (76%); $C_{11}H_8N_2O_3$ (216.2).

The hydantoin is treated with 10% strength sodium hydroxide solution at 100° C. for 30 hours, the mixture is then acidified to pH 2 with half-concentrated hydrochloric acid, while cooling with ice, and the pH is then brought back to 4.5 by means of 2N sodium hydroxide solution.

Yield: 11.3 g (60%); $C_{10}H_9NO_3$ (191.2).

NMR (DCOOD): $\delta = 5.66$ (s, 1H), 7.0 (d, 1H), 7.58 (dd, 1H), 7.76 (d, 1H), 7.91 (d, 1H) and 7.96 (d, 1H) ppm.

(d) DL-α-(t-Butyloxycarbonylamino-α-benzofur-5-yl)acetic acid (7d)

6.0 g (0.0314 mole) of 7c are stirred overnight analogously to Example 1e with 27.4 g (0.126 mole) of di-t-butyl dicarbonate in 60 ml of water, 60 ml of 2N sodium hydroxide solution and 120 ml of dioxane.

Yield: 6.6 g (73%); $C_{15}H_{17}NO_5$ (291.3).

NMR (DMSO): $\delta = 1.38$ (s, 9H), 5.22 (d, 1H), 7.0 (d, 1H), 7.38 (dd, 1H), 7.59 (d, 1H), 7.71 (s, 1H) and 8.04 (d, 2H) ppm.

(e) DL-7-(Benzofur-5-ylglycylamido)-3-chloro-3-cephem-4-carboxylic acid (7e)

2.0 g (6.86 mmol) of 7d are reacted analogously to Example 4d in tetrahydrofuran and dimethylformamide with 0.96 ml (6.86 mmol) of triethylamine, 3 drops of N-methylmorpholine, 0.89 ml (6.86 mmol) of isobutyl chloroformate and 1.77 g (7.55 mmol) of 7-ACCA.

Yield: 1.6 g (46%); $C_{22}H_{22}ClN_3O_7S$ (507.9).

1.6 g (3.15 mmol) of Boc-protected cephalosporin are deblocked analogously to Example 1g with TFA (+3 drops of anisole) and the product is freed from TFA with Amberlite IRA-68 (acetate form).

Yield: 0.9 g (65%); $C_{17}H_{14}ClN_3O_5S.2H_2O$ (443.9).

NMR (DCOOD): $\delta = 3.55-4.06$ (mm, 2H), 5.33–5.4 (dd, 1H), 5.75 (s, 1H), 5.9–6.0 (dd, 1H), 7.01 (s, 1H), 7.61 (m, 1H), 7.74–7.8 (m, 1H) and 7.92–7.98 (m, 2H) ppm.

EXAMPLE 8

D-7-(Benzofur-5-ylglycylamido)-3-chloro-3-cephem-4-carboxylic acid (8a) and L-form (8b)

Preparative HPLC resolution of 7e

Column: Zorbax Dupont 250-21,2 (ODS, 220 nm).

Mobile phase: 800 ml of $H_2O$-200 ml of acetonitrile-1 ml of TFA.

Amount applied: 0.7 g, in each case 30–50 mg in a 2 ml sample loop.

Flow: 12.5 ml/minute.

(b) L-form (peak I)

Yield: 186 mg; $C_{17}H_{14}ClN_3O_5S.CF_3COOH.H_2O$ (539.9).

|  |  |  |  |  |
|---|---|---|---|---|
| calculated: | C 42.27 | H 3.17 | S 5.94 | F 10.55 |
| found: | C 42.8 | H 3.2 | S 6.2 | F 9.5 |

NMR (DCOOD): $\delta = 3.73$ (d, J=18 Hz, 1H), 3.96 (d, J=18 Hz, 1H), 5.32 (d, J=5 Hz, 1H), 5.68 (s, 1H), 5.84 (d, J=5 Hz, 1H), 6.92 (s, 1H), 7.52 (d, J=8.0 Hz, 1H), 7.68 (d, J=8.0 Hz, 1H), 7.84 (s, 1H) and 7.9 (s, 1H) ppm.

(a) D-form (peak II)

Yield: 165 mg.
NMR (DCOOD): δ=3.5 (d, J=18 Hz, 1H), 3.84 (d, J=18 Hz, 1H), 5.25 (d, J=5 Hz, 1H), 5.65 (s, 1H), 5.9 (d, J=5 Hz, 1H), 6.92 (s, 1H), 7.5 (d, J=8 Hz, 1H), 7.68 (d, J=8 Hz, 1H), 7.84 (s, 1H) and 7.99 (s, 1H) ppm.

EXAMPLE 9

DL-7-(Benzofur-5-ylglycylamido)-3-methyl-3-cephem-4-carboxylic acid

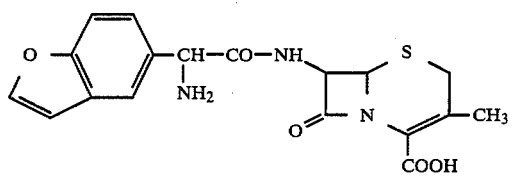

1 g (3.43 mmol) of 7d are reacted analogously to Example 3f in 16 ml of CH₂Cl₂ with 0.6 ml (3.43 mmol) of ethyl-diisopropylamine, 0.265 ml (3.43 mmol) of methanesulphonyl chloride and 0.927 g (3.43 mmol) of t-butyl 7-amino-3-methyl-3-cephem-4-carboxylic acid, which is dissolved in 14 ml of CH₂Cl₂ in the presence of 0.597 ml (3.43 mmol) of ethyldiisopropylamine.
Yield: 1.1 g (59%); C₂₇H₃₃N₃O₇S (543.6).

1.1 g (2 mmol) of Boc-protected cephalosporin are deblocked analogously to Example 3f and freed from TFA on an Amberlite IRA-68 column (acetate form).
Yield: 350 mg (42%); C₁₈H₁₇N₃O₅S.2H₂O (411.4).
NMR (/DCOOD): δ-2.2 (d, 3H), 3.22-3.64 (mm, 2H), 5.18-5.24 (dd, 1H), 5.70 (d, 1H), 5.78-5.88 (dd, 1H), 6.97 (m, 1H), 7.56 (d, 1H), 7.69-7.76 (m, 1H), 7.88 (m, 1H) and 7.94 (s, 1H) ppm.

EXAMPLE 10

DL-7-(2,1-8enzisothiazol-6-ylglycylamido)-3-methyl-3-cephem-4-carboxylic acid

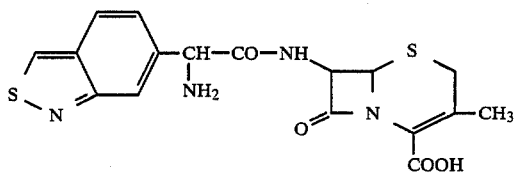

(a) Methyl 2,1-benzisothiazole-6-carboxylate (10a)

51.6 g (0.365 mole) of N-sulphinylmethanesulphonamide in 50 ml of benzene are added to a solution of 60 g (0.298 mole) of methyl 3-sulphinylamino-4-methyl-benzoate in 200 ml of benzene at room temperature under argon. Thereafter, 24.9 g (0.315 mole) of pyridine, dissolved in 75 ml of benzene, are added in portions to the reaction mixture, while cooling with ice. The mixture is subsequently stirred at 0° C. for 10 minutes and then heated under reflux for 45 hours. After cooling, the benzene and pyridine are distilled off in vacuo, the oil which remains is poured into 150 ml of water and the mixture is acidified to pH 4 with 2N HCl. A brown solid thereby forms from the oil, and is extracted with chloroform. The chloroform extracts are washed with water, dried over MgSO₄ and concentrated to dryness. The oil which remains crystallizes to a brown-yellow material by adding n-hexane, and the material is filtered off with suction and washed with n-hexane.
Yield: 44.1 g (80%); C₉H₇NO₂S (193.2).

| calculated: | C 55.9 | H 3.7 | N 7.2 | S 16.6 |
| found: | C 55.9 | H 3.7 | N 7.3 | S 16.7 |

After chromatography on silica gel with the mobile phase petroleum ether/ethyl acetate (5:1), 32.9 g (60%) of pure product are obtained.
NMR (CDCl₃): δ=3.98 (s, 3H), 7.84 (d, 2H), 8.6 (s, 1H) and 9.28 (s, 1H) ppm.

(b) 6-Hydroxymethyl-2,1-benzisothiazole (10b)

5.8 g (0.03 mole) of 10a are stirred analogously to Example 1a in 80 ml of tetrahydrofuran with 58.8 ml (0.09 mole) of DIBAL (1.53 molar solution in toluene) at −60° C. to −70° C. overnight.
Yield: 4.2 g (85%); C₈H₇NOS (165.2).
NMR (DMSO): δ=4.62 (s, 2H), 5.44 (broad s, 1H), 7.25 (d, 1H), 7.72 (s, 1H), 7.9 (d, 1H) and 9.74 (s, 1H) ppm.

(c) 2,1-Benzisothiazole-6-carboxaldehyde (10c)

1.65 g (10 mmol) of 10b are stirred analogously to Example 1b in 100 ml of CH₂Cl₂ and 30 ml of tetrahydrofuran with 5.5 g (63.4 mmol) of manganese(IV) oxide at room temperature overnight.
Yield: 1.45 g (89%); C₈H₅NOS (163.2).
NMR (DMSO): δ=7.66 (dd, 1H), 8.08 (d, 1H), 8.5 (s, 1H), 9.93 (s, 1H) and 10.18 (s, 1H) ppm.

(d) 5-(2,1-Benzisothiazol-6-yl)-2,4-imidazolidinedione (10d)

18.6 g (0.114 mole) of 10c are stirred analogously to Example 1c in ethanol, methanol and water with 8.4 g (0.171 mole) of sodium cyanide and 43.8 g (0.456 mole) of ammonium carbonate at 60° C. for 16 hours.
Yield: 19.8 g (75%); C₁₀H₇N₃O₂S (233.2).

| calculated: | C 51.49 | H 3.02 | N 18.01 | S 13.74 |
| found: | C 50.6 | H 3.2 | N 18.0 | S 13.2 |

NMR (DMSO): δ=5.38 (s, 1H), 7.25 (dd, 1H), 7.80 (s, 1H), 7.98 (d, 1H), 8.57 (s, 1H), 9.81 (s, 1H) and 10.96 (s, 1H) ppm.

(e) DL-α-Amino-α-(2,1-benzisothiazol-6-yl)acetic acid (10e)

16.5 g (0.071 mole) of 10d are heated under reflux analogously to Example 3e with 17.0 g (0.71 mole) of lithium hydroxide in 250 ml of water for 20 hours.
Yield: 12.1 g C₉H₈N₂O₂S (208.2; contains 12% of LiCl, 4.7% of HCl and 8.8% of H₂O).

| calculated: | C 37.7 | H 2.8 | N 9.8 | | |
| found: | C 37.7 | H 4.2 | N 10.4 | Cl 14.7 | Li 2.0 |

NMR (DMSO): δ=4.5 (s, 1H), 7.42 (dd, 1H), 7.86 (s, 1H), 7.9 (s, 1H) and 9.8 (s, 1H) ppm.

(f) DL-α-t-Butyloxycarbonylamino-α-(2,1-benzisothiazol-6-yl)acetic acid (10f)

8.2 g (39.4 mmol) of 10e are stirred analogously to Example 3e with 17.2 g (78.8 mmol) of di-tert.-butyl dicarbonate and 6.64 g (79 mmol) of sodium bicarbonate in 140 ml of water and 140 ml of dioxane at room temperature overnight.

Yield: 6.8 g (56%; ethyl acetate/petroleum ether). $C_{14}H_{16}N_2O_4S$ (308.4)

NMR (DMSO): δ=1.41 (s, 9H), 5.32 (d, 1H), 7.38 (d, 1H), 7.78–7.85 (s and d, 2H), 7.94 (d, 1H) and 9.8 (s, 1H) ppm.

(g) DL-7-(2,1-Benzisothiazol-6-ylglycylamido)-3-methyl-3-cephem-4-carboxylic acid (10g)

2 g (6.5 mmol) of 10f are reacted with 1.13 ml (6.5 mmol) of ethyl diisopropylamine, 0.503 ml (6.5 mmol) of methanesulphonyl chloride and 1.76 g (6.5 mmol) of t-butyl 7-amino-3-methyl-3-cephem-4-carboxylate, which is dissolved in 32 ml of $CH_2Cl_2$ with 1.13 ml (6.5 mmol) of ethyl diisopropylamine, in 32 ml of $CH_2Cl_2$ and 2 ml of tetrahydrofuran.

Yield: 3 g (83%); $C_{26}H_{32}N_4O_6S_2$ (560.7).

2.9 g (5.17 mmol) of Boc-protected cephalosporin are deblocked analogously to Example 3f and converted into the betaine by means of Amberlite IRA-68 (acetate form).

Yield: 1.3 g (57%); $C_{17}H_{16}N_4O_4S_2 \cdot 2H_2O$ (440.5).

NMR (DCOOD): δ=2.17 (d, 3H), 3.21–3.64 (mm, 2H), 5.16–5.25 (dd, 1H), 5.76–5.86 (dd, 1H), 5.8 (d, 1H), 7.59 (d, 1H), 8.14–8.20 (q, 1H), 8.26 (s, 1H) and 9.88 (s, 1H) ppm.

EXAMPLE 11

DL-6-(lndol-4-ylglycylamido)-penicillanic acid

(a) DL-α-(Benzyloxycarbonylamino-α-indol-4-yl) acetic acid (11a)

10 g (44.2 mol) of 4b are suspended in 200 ml of $H_2O$ and the pH is brought to 9 with 2N sodium hydroxide solution. The clear solution is cooled to 50° C. and 9.8 ml (69 mmol) of benzyl chloroformate are added dropwise in the course of 30 minutes, with simultaneous addition of 2N sodium hydroxide solution (pH 8–10). After the mixture has been stirred at 20° C. for 2 hours (pH 9.0), it is extracted once with ether and the aqueous phase is acidified to pH 2 with 2N HCl and extracted with ethyl acetate. After washing with sodium chloride solution, drying over $Na_2SO_4$ and distilling off the ethyl acetate, the residue is crystallized from ether/petroleum ether.

Yield: 11.9 g; $C_{18}H_{15}N_2O_4$ (323.3).

NMR (DMSO): δ=5.07 (s, 2H), 5.56 (d, 1H), 6.55 (s, 1H), 7.0–7.12 (m, 2H), 7.34–7.42 (m, 7H), 8.03 (d, 1H) and 11.24 (s, 1H) ppm.

(b) DL-6-[2-(Benzyloxycarbonylamino)-indol-4-ylglycylamido]penicillanic acid (11b)

5 g (15.5 mmol) of 11a are reacted analogously to Example 4d with 2.17 ml (15.5 mmol) of triethylamine, 3 drops of N-methylmorpholine, 1.49 ml (15.5 mmol) of ethyl chloroformate and 3.7 g (17.1 mmol) of 6-aminopenicillanic acid, which is suspended in 30 ml of $H_2O$ and 50 ml of tetrahydrofuran and dissolved with 0.5N sodium hydroxide solution, in 50 ml of tetrahydrofuran and 25 ml of dimethyl formamide.

Yield: 5.9 g (73%); $C_{26}H_{26}N_4O_6S$ (522.6).

| | | | | |
|---|---|---|---|---|
| calculated: | C 59.8 | H 5.0 | N 10.7 | S 6.1 |
| found: | C 58.9 | H 5.4 | N 9.6 | S 5.3 |

(c) Sodium DL-6-(indol-4-ylglycylamido)penicillanate (11c)

Hydrogen is allowed to flow through a suspension of 20 g of palladium black in 200 ml of water for 1 hour and 5.7 g (10.9 mmol) of 11b, which have first been converted into the sodium salt with 0.1N sodium hydroxide solution in acetone/water, are then added. The suspension is flushed with hydrogen for 3 hours, the catalyst is then separated off and washed with water and the filtrate is concentrated to dryness. The residue is dissolved in $H_2O$, the pH is brought to 1.8 with 2N HCl and the solution is extracted with ethyl acetate. The aqueous phase is lyophilized, the lyophilisate is suspended in 300 ml of $CH_2Cl_2$, the suspension is cooled to −10° C. and 2.9 ml of triethylamine are added. The solution is dried with $Na_2SO_4$ and the filtrate is treated with 12 ml of a 1M solution of sodium 2-ethyl-hexanoate in ether/methanol. After addition of ether, a precipitate separates out, and is filtered off with suction and dried in vacuo.

Yield: 0.4 g; $C_{18}H_{19}NNaO_4S$ (410.4).

NMR (DMSO): δ=1.56 (dd, 6H), 3.96 (d, 1H), 4.81 (d, 1H), 5.46 (dd, 2H), 6.63 (m, 1H), 6.97–7.08 (m, 2H), 7.31–7.36 (m, 2H), 8.77 (broad s, 1H) and 11.24 (broad s, 1H) ppm.

It will be understood that the specification and examples are illustrative but not limitative of the present invention and that other embodiments within the spirit and scope of the invention will suggest themselves to those skilled in the art.

What is claimed:

1. A β-lactam compound of the formula in which

X represents a radical of the fomula wherein

R[5] represents hydrogen, or represents halogen, azido or represents vinyl, 1-propenyl, 1-butenyl or straight-chain, branched or cyclic alkyl which has up to 10 C atoms and is optionally substituted by halogen, alkoxy or alkylthio with in each case up to 8 C atoms, halogenoalkylthio and halogenoalkoxy with in each case up to 8 C atoms, nitro, cyano, an amino group, aryl, SO$_3$H, SO$_2$NH$_2$, SO$_2$-alkyl with up to 6 C atoms, OH, SH, acyloxy or acylthio with in each case up to 7 C atoms, OCONH$_2$, carboxyl, alkoxycarbonyl with up to 8 C atoms, phenylthio, benzyloxy and/or benzylthio, by a pyridinium radical, or by a radical of the formula

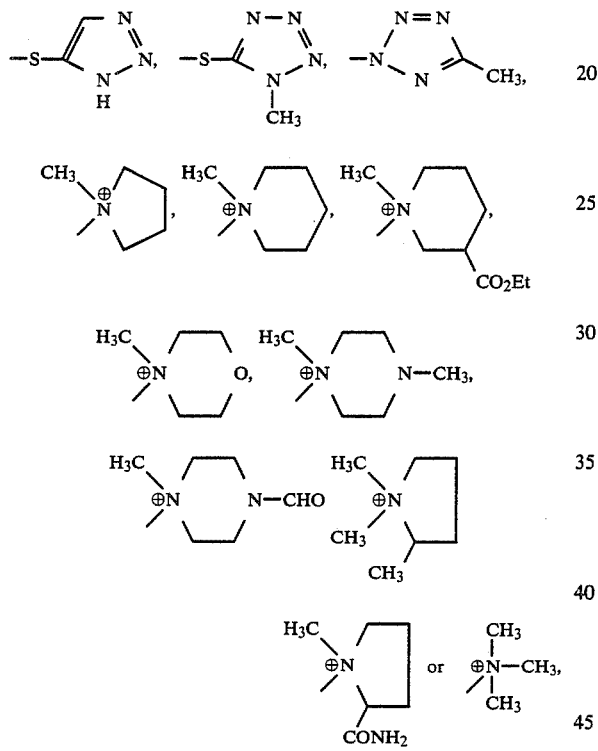

or represents alkoxy or alkylthio with up to 5 C atoms,

R[1] represents a radical of the formula

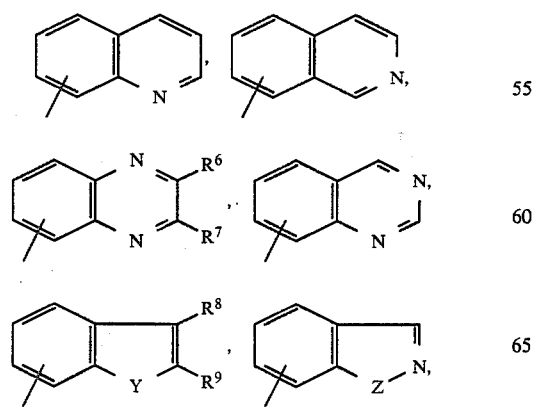

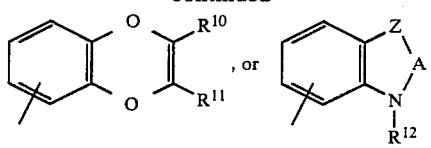

which is optionally mono-, di-, tri- or tetra-substituted by halogen, alkyl, alkoxy, alkylthio, halogenoalkyl, halogenoalkoxy or halogenoalkylthio with in each case up to 8 C atoms, nitro, cyano or phenyl, wherein R[6] and R[7] are identical or different and represent hydrogen, or represent C$_6$-C$_{10}$-aryl, or represent an amino group, or represent hydroxyl, or represent alkoxy with up to 8 C atoms, or represent acyl or acyloxy with in each case up to 7 C atoms, or represent alkyl with up to 12 C atoms, R[8] and R[9] are identical or different and represent hydrogen, or represent C$_6$-C$_{10}$-aryl, or represent heterocyclyl, or represent hydroxyl, or represent an amino group, or represent alkoxy with up to 8 C atoms, or represent acyl with up to 7 C atoms, or represent acyloxy with up to 7 C atoms, or represent alkoxycarbonyl with up to 8 C atoms, or represent alkyl with up to 12 C atoms, or R[8] and R[9] together represent the group

R[10] and R[11] are identical or different and represent hydrogen, or represent alkyl with up to 12 C atoms, or represent C$_6$-C$_{10}$-aryl, or represent alkoxycarbonyl with up to 8 C atoms, Y represents oxygen or —N—R[12], Z represents oxygen, sulphur or —N—R[13], A represents the group

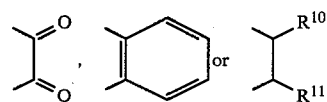

and wherein

R[12] and R[13] are identical or different and represent hydrogen, or represent C$_6$-C$_{10}$-aryl, or represent straight-chain, branched or cyclic alkyl with up to 8 C atoms, R[2] represents hydrogen or represents an amino-protective group, R[3] represents hydrogen, or represents alkoxy or alkylthio with in each case up to 5 C atoms, or represents an amino group, or represents NHCHO, and R[4] represents hydrogen, or represents a carboxyl-protective group, or represents alkali metal ions or ammonium ions, or represents a radical of the formula

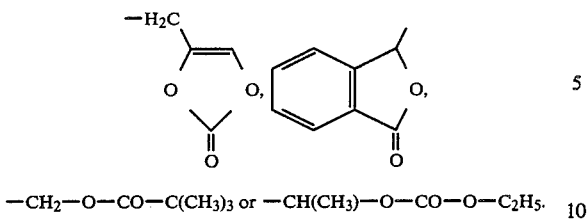

—CH₂—O—CO—C(CH₃)₃ or —CH(CH₃)—O—CO—O—C₂H₅.

2. A β-lactam compound according to claim 1, wherein R² represents an amino-protective group selected from the group consisting of tert.-butoxycarbonyl, carbobenzoxy, 2-methoxycarbonyl-1-methylvinyl, trityl, benzyl, benzyloxycarbonyl, formyl and chloroacetyl.

3. A β-lactam compound according to claim 1, wherein R⁴ represents a carboxyl-protective group selected from the group consisting of tert.-butyl, decyl, 2,2,2-trichloroethyl, benzyl, 4-methoxybenzyl, 4-nitrobenzyl, triphenylmethyl, diphenylmethyl, acetoxymethyl, pivaloyloxymethyl, allyl and trimethylsilyl.

4. A β-lactam compound according to claim 1, wherein aryl when present as a phenyl ring.

5. A β-lactam compound according to claim 1, wherein alkyl when present, unless otherwise defined, is a straight-chain, branched or cyclic, alkyl radical with up to 10 C atoms optionally substituted by halogen, alkoxy or alkylthio with in each case up to 8 C atoms, halogenoalkylthio and halogenoalkoxy with in each case up to 8 C atoms, nitro, cyano, an amino group, aryl, SO₃H, SO₂NH₂, SO₂-alkyl with up to 6 C. atoms, OH, SH, acyloxy or acylthio with in each case up to 7 C atoms, OCONH₂, carboxyl, alkoxycarbonyl with up to 8 C atoms, phenylthio, benzyloxy and/or benzylthio.

6. A β-lactam compound according to claim 1, wherein the amino group when present is of the formula

wherein
R¹⁴ and R¹⁵ are identical or different and represent hydrogen, or represent alkyl with up to 10 C atoms, or represent C₆–C₁₀-aryl, or represent C₇–C₁₄-aralkyl, or represent acyl with up to 10 C atoms.

7. A β-lactam compound according to claim 1, in which
R⁵ represents hydrogen, or represents fluorine, chlorine or bromine, or represents straight-chain, branched or cyclic alkyl which has up to 4 C atoms and is optionally substituted by one or more radicals from the group consisting of fluorine chlorine, bromine, alkoxy and alkylthio with in each case up to 3 C atoms, OCONH₂ and acyloxy with up to 4 C atoms, or by a radical of the formula

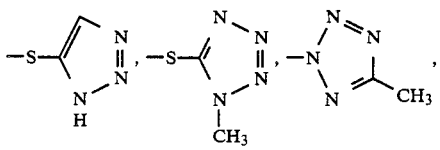

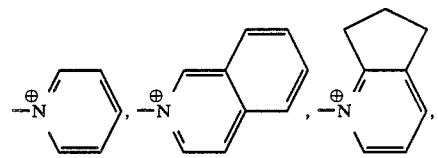

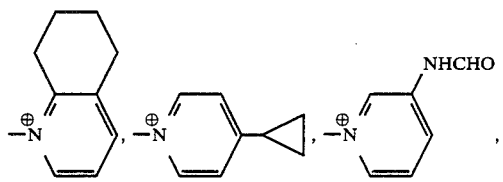

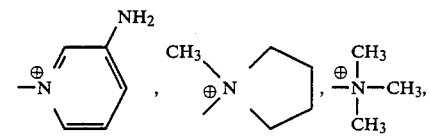

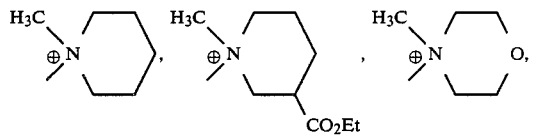

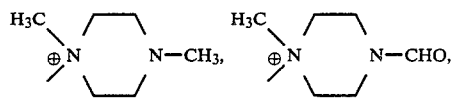

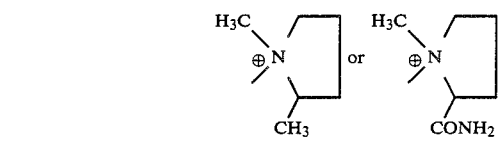

or represents alkoxy or alkylthio with in each case up to 3 C atoms,
R¹ represents a radical of the formula

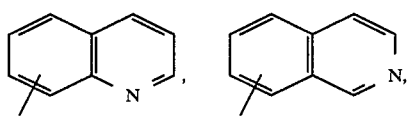

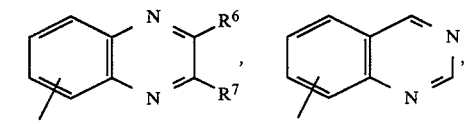

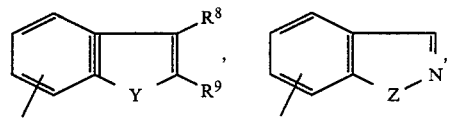

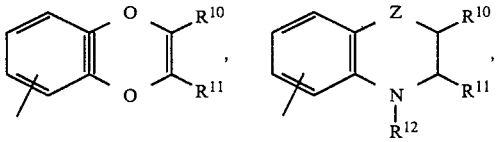

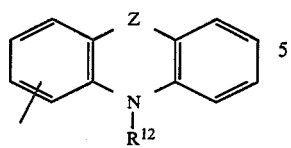

which is optionally mono-, di-, tri- or tetra-substituted by halogen, alkyl, alkoxy, alkylthio, halogenoalkyl, halogenoalkoxy or halogenoalkylthio with in each case up to 8 C atoms, nitro, cyano or phenyl, wherein $R^6$ and $R^7$ are identical or different and represent hydrogen, or represent phenyl, or represent an amino group, or represent hydroxyl, or represent alkoxy with up to 6 C atoms, or represent benzoyloxy or alkanoyloxy with up to 4 C atoms, or represent alkyl which has up to 8 C atoms, $R^8$ and $R^9$ are identical or different and represent hydrogen, or represent phenyl, or represent hydroxyl, or represent pyridyl, thienyl, furyl or pyrimidyl, or represent an amino group, or represent alkoxy with up to to 6 C atoms, or represent benzoyloxy or alkanoyloxy with up to 4 C atoms, or represent benzoyl or acetyl, or represent alkoxycarbonyl with up to 6 C atoms, or represent alkyl which has up to 8 C atoms, or $R^8$ and $R^9$ together represent the group

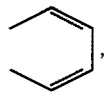

$R^{10}$ and $R^{11}$ are identical or different and represent hydrogen, or represent alkyl which has up to 8 C atoms, or represent phenyl, or represent alkoxycarbonyl with up to 6 C atoms, Y represents oxygen or $-N-R^{12}$, Z represents oxygen, sulphur or $-NR^{13}$, and wherein $R^{12}$ and $R^{13}$ are identical or different and represent hydrogen, or represent phenyl, or represent straight-chain, branched or cyclic alkyl with up to 6 C atoms, $R^2$ represents hydrogen or represents an aminoprotective group, $R^3$ represents hydrogen, or represents alkoxy or alkylthio with in each case up to 3 C atoms, or represents an amino group, or represents NHCHO, and $R^4$ represents hydrogen, or represents a carboxylprotective group, or represents sodium, potassium, lithium or ammonium ions, or represents a radical of the formula

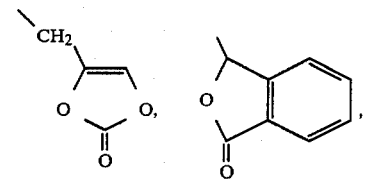

$CH_2-O-CO-C(CH_3)_3$ or $-OH(CH_3)-O-CO-O-C_2H_5$.

8. A β-lactam compound according to claim 1 in which $R^5$ represents hydrogen, or represents chlorine or fluorine, or represents methyl, methoxy, methylthio, trifluoromethyl or methoxymethyl, or represents vinyl, $-CH=CH-CH_3$, $-CH=CH-C_2H_5$, $-CH=CH-CH_2Cl$,

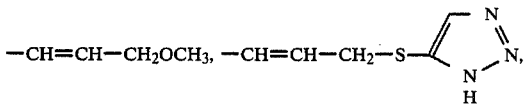

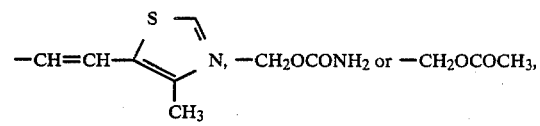

or represents a radical of the formula

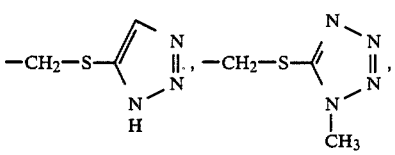

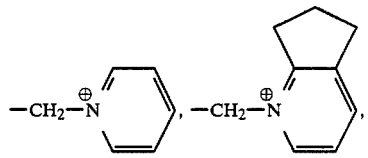

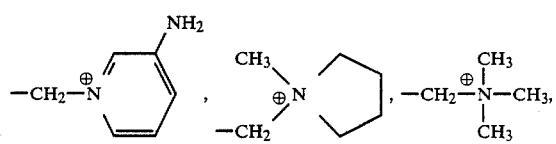

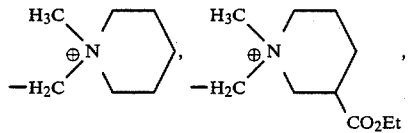

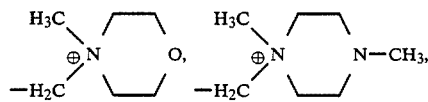

-continued

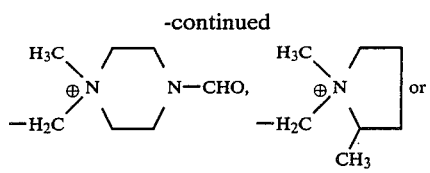

R¹ represents a radical of the formula

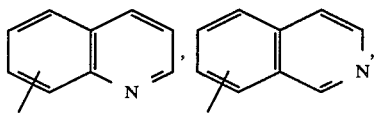

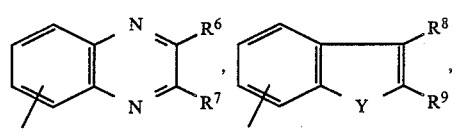

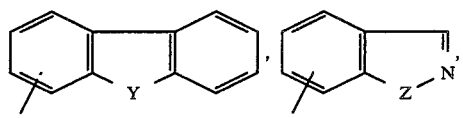

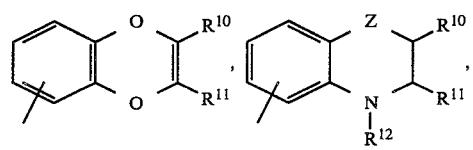

which is optionally mono-, di-, tri- or tetra-substituted by halogen, alkyl, alkoxy, alkylthio, halogenoalkyl, halogenoalkoxy or halogenoalkylthio with in each case up to 8 C atoms, nitro, cyano or phenyl, wherein $R^6$ and $R^7$ are identical or different and represent hydrogen, or represent phenyl, or represent amino, methylamino, dimethylamino, phenylamino, or represent hydroxyl, or represent alkoxy with up to 4 C atoms, or represent benzoyloxy or acetyloxy, or represent alkyl which has up to 6 C atoms, $R^8$ and $R^9$ are identical or different and represent hydrogen, or represent phenyl, or represent pyridyl, thienyl, furyl or pyrimidyl, or represent hydroxyl, or represent amino, methylamino, dimethylamino, phenylamino, or represent alkoxy with up to 4 C atoms, or represent benzoyloxy or acetyloxy, or represent benzoyl or acetyl, or represent alkoxycarbonyl with up to 4 C atoms, or represent alkyl which has up to 6 C atoms, $R^{10}$ and $R^{11}$ are identical or different and represent hydrogen, or represent alkyl which has up to 6 C atoms, or represent phenyl, or represent alkoxycarbonyl with up to 4 C atoms, Y represents oxygen or $NR^{12}$, Z represents oxygen, sulphur or $-NR^{13}$, and wherein $R^{12}$ and $R^{13}$ are identical or different and represent hydrogen, or represent phenyl, or represent straight-chain or branched alkyl with up to 4 C atoms, $R^2$ represents hydrogen, or represents an aminoprotective group, $R^3$ represents hydrogen, or represents methoxy or methylthio, or represents amino, alkylamino or dialkylamino, alkyl with in each case up to 3 C atoms, phenylamino, benzylamino, or represents NHCHO, and $R^4$ represents hydrogen, or represents a carboxyl-protective group, or represents sodium, potassium, lithium or ammonium ions, or represents a radical of the formula

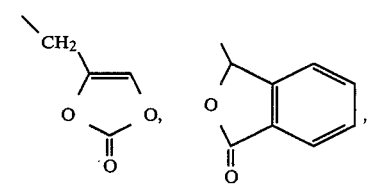

9. A β-lactam compound according to claim 1, wherein such compound is 7-(indol-4-ylglycylamido)-3-chloro-3-cephem-4-carboxylic acid of the formula

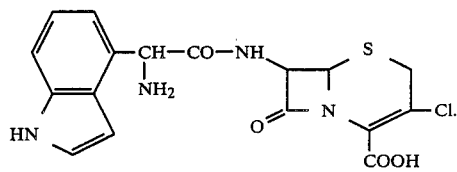

10. A β-lactam compound according to claim 1, wherein such compound is 7-(indol-5-ylglycylamido)-3-chloro-3-cephem-4-carboxylic acid of the formula

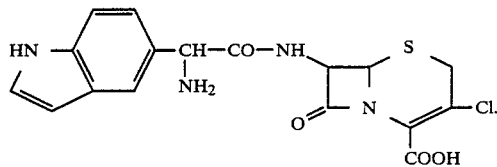

11. A β-lactam compound according to claim 1, wherein such compound is 7-(benzofur-5-ylglycylamido)-3-chloro-3-cephem-4-carboxylic acid of the formula

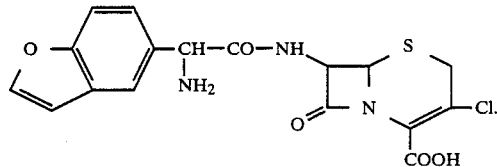

12. A β-lactam compound according to claim 1, wherein such compound is 7-(benzofur-5- ylglycylamido)-3-methyl-3-cephem-4-carboxylic acid of the formula

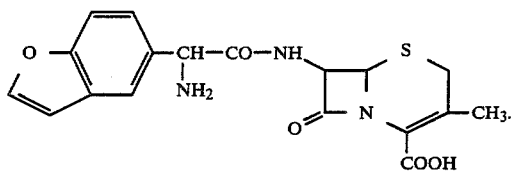

13. A β-lactam compound according to claim 1, wherein such compound is 6-(indol-4-ylglycylamido)-penicillanic acid of the formula

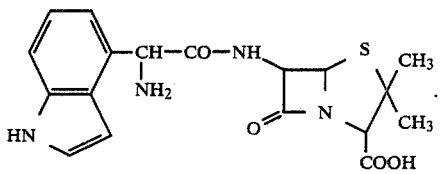

14. An antibacterial composition comprising an antibacterially effective amount of a β-lactam compound according to claim 1 in admixture with a pharmaceutically acceptable diluent.

15. A unit dose of a composition according to claim 14 in the form of a tablet, capsule or ampule.

16. A method of combating bacterial diseases in a patient which comprises administering to a patient in need thereof an antibacterially effective amount of a β-lactam compound according to claim 1.

17. The method according to claim 16, wherein such β-lactam compound is
7-(indol-4-ylglycylamido)-3-chloro-3-cephem-4-carboxylic acid,
7-(indol-5-ylglycylamido)-3-chloro-3-cephem-4-carboxylic acid,
7-(benzofur-5-ylglycylamido)-3-chloro-3-cephem-4-carboxylic acid,
7-(benzofur-5-ylglycylamido)-3-methyl-3-cephem-4-carboxylic acid or
6-(indol-4-ylglycylamido)-penicillanic acid.

18. An animal feed or feed pre-mix comprising a growth promoting amount of a β-lactam compound according to claim 1 and an edible carrier.

19. A method of promoting the growth of an animal which comprises feeding said animal a growth promoting amount of a β-lactam compound according to claim 1.

20. The method according to claim 19, wherein such β-lactam compound is
7-(indol-4-ylglycylamido)-3-chloro-3-cephem-4-carboxylic acid,
7-(indol-5-ylglycylamido)-3-chloro-3-cephem-4-carboxylic acid,
7-(benzofur-5-ylglycylamido)-3-chloro-3-cephem-4-carboxylic acid,
7-(benzofur-5-ylglycylamido)-3-methyl-3-cephem-4-carboxylic acid or
6-(indol-4-ylglycylamido)-penicillanic acid.

* * * * *

UNITED STATES PATENT AND TRADEMARK OFFICE
CERTIFICATE OF CORRECTION

PATENT NO. : 4,734,407
DATED     : Mar. 29, 1988
INVENTOR(S) : Schmidt et al.

It is certified that error appears in the above-identified patent and that said Letters Patent is hereby corrected as shown below:

| | |
|---|---|
| Col. 3, line 17 | Insert --and-- after "NHCHO" |
| Col. 43, line 25 | Delete "as" and substitute --is-- |
| Col. 46, line 11 | Delete "O" in third instance and substitute --C-- |
| Col. 48, line 28 | Insert -- $-CH_2-O-CO-C(CH_3)_3$ or $-CH(CH_3)-O-CO-O-C_2H_5$ -- after formula |

Signed and Sealed this

Twenty-fifth Day of October, 1988

Attest:

DONALD J. QUIGG

Attesting Officer

Commissioner of Patents and Trademarks